US008183415B2

(12) United States Patent
Thiel et al.

(10) Patent No.: US 8,183,415 B2
(45) Date of Patent: May 22, 2012

(54) METHODS OF SYNTHESIZING CINACALCET AND SALTS THEREOF

(75) Inventors: Oliver Thiel, Camarillo, CA (US); Charles Bernard, Moorpark, CA (US); Robert Larsen, Newbury Park, CA (US); Michael John Martinelli, Thousand Oaks, CA (US); Masooma Tamim Raza, Woodland Hills, CA (US)

(73) Assignee: Amgen, Inc., Thousand Oaks, CA (US)

( * ) Notice: Subject to any disclaimer, the term of this patent is extended or adjusted under 35 U.S.C. 154(b) by 0 days.

(21) Appl. No.: 13/109,538

(22) Filed: May 17, 2011

(65) Prior Publication Data

US 2011/0281954 A1    Nov. 17, 2011

Related U.S. Application Data

(63) Continuation of application No. 12/142,450, filed on Jun. 19, 2008, now abandoned.

(60) Provisional application No. 60/945,443, filed on Jun. 21, 2007.

(51) Int. Cl.
*C07C 209/70* (2006.01)
*C07C 209/68* (2006.01)

(52) U.S. Cl. ........ 564/337; 564/219; 564/374; 564/387; 560/28

(58) Field of Classification Search .................. None
See application file for complete search history.

(56) References Cited

U.S. PATENT DOCUMENTS

| | | | |
|---|---|---|---|
| 5,110,948 A | 5/1992 | Marks et al. |
| 5,342,909 A | 8/1994 | Grubbs et al. |
| 6,011,068 A | 1/2000 | Nemeth et al. |
| 6,031,003 A | 2/2000 | Nemeth et al. |
| 6,211,244 B1 | 4/2001 | Van Wagenen et al. |
| 6,313,146 B1 | 11/2001 | Van Wagenen et al. |
| 6,313,365 B1 | 11/2001 | Hori et al. |
| 6,316,380 B1 | 11/2001 | Nolan et al. |
| 6,362,357 B1 | 3/2002 | Nolan et al. |
| 6,369,265 B1 | 4/2002 | Nolan et al. |
| 6,403,801 B1 | 6/2002 | Nolan et al. |
| 6,403,802 B1 | 6/2002 | Nolan et al. |
| 6,417,363 B1 | 7/2002 | Van Der Schaaf et al. |
| 6,426,419 B1 | 7/2002 | Grubbs et al. |
| 6,500,975 B1 | 12/2002 | Schwab et al. |
| 6,583,307 B2 | 6/2003 | Nolan et al. |
| 6,586,599 B1 | 7/2003 | Nolan et al. |
| 6,610,626 B2 | 8/2003 | Grubbs et al. |
| 6,613,910 B2 | 9/2003 | Grubbs et al. |
| 6,620,955 B1 | 9/2003 | Pederson et al. |
| 6,635,768 B1 | 10/2003 | Hermann et al. |
| 6,800,170 B2 | 10/2004 | Kendall et al. |
| 6,803,429 B2 | 10/2004 | Morgan et al. |
| 6,818,586 B2 | 11/2004 | Grubbs et al. |
| 6,844,442 B2 | 1/2005 | Milstein et al. |
| 6,867,303 B2 | 3/2005 | Grela |
| 6,900,347 B2 | 5/2005 | Paulson et al. |
| 7,026,495 B1 | 4/2006 | Pederson et al. |
| 7,071,357 B2 | 7/2006 | Landis et al. |
| 7,173,157 B2 | 2/2007 | Takai et al. |
| 7,205,424 B2 | 4/2007 | Nolan |
| 7,393,967 B2 * | 7/2008 | Lifshitz-Liron ............... 560/41 |
| 2006/0199728 A1 | 9/2006 | Hartwig et al. |

FOREIGN PATENT DOCUMENTS

| | | |
|---|---|---|
| WO | WO 92-20642 | 11/1992 |
| WO | WO 02-40491 | 5/2002 |
| WO | WO 2005/034928 | 4/2005 |
| WO | WO 2006/125026 | 11/2006 |
| WO | WO 2006/127941 | 11/2006 |
| WO | WO 2007/112280 | 5/2007 |
| WO | WO 2007/062147 | 10/2007 |
| WO | WO 2007/127445 A2 | 11/2007 |
| WO | WO 2008/117299 A1 | 10/2008 |
| WO | WO 2009/002427 | 12/2008 |

OTHER PUBLICATIONS

Ahmed, et al., *J. Am. Chem. Soc.*, 125, 2003, p. 10311.
Briggs, et al., *Org. Lett.*, 7, 2005, p. 4795.
Communication pursuant to Rule 114(2) EPC, for the corresponding European Application No. 08768607.7, dated Jan. 10, 2011 (3 pages).
The International Search Report for the corresponding International Application No. PCT/US2008/007621, dated Jun. 23, 2009 (6 pages).
The PCT form PCT/ISA/206, for the corresponding International Application No. PCT/US2008/007621, which includes the Communication Relating to the Results of the Partial International Search, dated Apr. 7, 2009. (6 pgs.).
Database CAPLUS on STN, Acc. No. 2007:1274895, LIFSHITZ-LIRON, WO 2007127449 A1 (Nov. 8, 2007) (abstract).
De Brabander, et al., *Tetrahedron*, 60, 2004, p. 9635.
Hayashi, et al., *Chem. Rev.*, 103, 2003, pp. 2829-2844.
Kabalka, et al., J. Org. Chem, 49, 1984, p. 1656.
Kim, et al., *Synlett*, 3, 1998, pp. 261-262.
Lautens, et al., *Synthesis*, 12, 2004, pp. 2006-2014.
Lu, et al., *J. Org. Chem*, 70, 2005, pp. 9561-9653.
Mellegaard-Waetzig, et al., *Synlett*, 18, 2005, pp. 2759-2762.
Miyaura, et al., Chem. Reviews, 1995, pp. 2457-2483.
Sakuma, et al., *J. Org. Chem.*, 66, 2001, pp. 8944-8946.

* cited by examiner

*Primary Examiner* — Brian J Davis

(74) *Attorney, Agent, or Firm* — Fitzpatrick, Cella, Harper & Scinto

(57) ABSTRACT

Methods of preparing cinacalcet, cinacalcet derivatives, and salts thereof is disclosed herein. Also disclosed herein are polymorphs of cinacalcet, compositions of cinacalcet, and methods of treating a subject by administering cinacalcet, wherein cinacalcet is prepared by the disclosed methods.

14 Claims, No Drawings

METHODS OF SYNTHESIZING CINACALCET AND SALTS THEREOF

The present application is a continuation of U.S. patent application Ser. No. 12/142,450 that was filed on Jun. 19, 2008 now abandoned, and it claims the benefit of priority of U.S. Provisional Patent Application No. 60/945,443 that was filed on Jun. 21, 2007.

FIELD OF THE INVENTION

Background of the Invention

Sensipar® (cinacalcet) is a calcimimetic agent that has the chemical name N-[1-(R)-(−)-(1-naphthyl)ethyl]-3-[3-(trifluoromethyl)phenyl]-1-aminopropane hydrochloride, has the empirical formula $C_{22}H_{22}F_3N \cdot HCl$, and has the structural formula

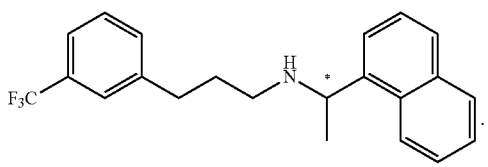

The molecular weight of the hydrochloride salt is 393.9 g/mol and the free base is 357.4 g/mol. There is one chiral center in the molecule (marked with a *), and the R enantiomer is the more potent enantiomer.

Cinacalcet hydrochloride is commercially available as Sensipar® and Mimpara®. The calcimimetic agent is used to increase the sensitivity of the calcium-sensing receptor to activation by extracellular calcium. This calcimimetic has been shown to be therapeutically effective in the treatment of patients with chronic kidney disease on dialysis who have secondary hyperparathyroidism and of hypercalcemia in patients with parathyroid carcinoma. Today there are more than 300,000 kidney dialysis patients with chronic kidney disease (CKD) in the U.S. alone. Nearly all of these patients suffer from secondary hyperparathyroidism (HPT), which is a progressive disease, associated with increases in parathyroid hormone (PTH) levels and abnormal calcium and phosphorus metabolism. In a typical patient having mild HPT, the serum intact parathyroid hormone (iPTH) levels are 300 to 500 pg/ml; a patient having moderate HPT has an iPTH of 500 to 800 pg/ml; and a patient with severe HPT has an iPTH of greater than 800 pg/ml. A normal iPTH level should be in the range of about 250 pg/ml. The lower limit of normal calcium level in humans is about 8.4 mg/dL. HPT can develop early during the course of CKD and continues to progress as kidney function declines. Untreated secondary HPT is characterized by abnormal calcium and phosphorus levels and is associated with serious consequences, including cardiovascular morbidity.

Increased PTH stimulates osteoclastic activity resulting in cortical bone resorption and marrow fibrosis. Sensipar® is the first treatment that meets a significant medical need in patients with secondary HPT to lower the levels of PTH, calcium, and phosphorus in the blood, in order to prevent progressive bone disease and the systemic consequences of disordered mineral metabolism. Reduction of PTH levels in CKD patients on dialysis with uncontrolled secondary HPT has been shown to have positive effects on bone-specific alkaline phosphatase (BALP), bone turnover and bone fibrosis.

PTH secretion is regulated through the action of a calcium-sensing receptor on the cell surface of the parathyroid gland. Sensipar® directly lowers PTH levels by increasing the sensitivity of this calcium-sensing receptor to extracellular calcium. The reduction in PTH is associated with a concomitant decrease in serum calcium levels.

Sensipar® allows practitioners to reduce PTH while lowering calcium-phosphorus product, which is consistent with the National Kidney Foundation's Kidney Disease Outcomes Quality Initiative (K/DOQI) clinical practice guidelines for bone metabolism and disease in chronic kidney disease. Prior to its development, the only available medical treatments for patients with secondary HPT were phosphate binders and vitamin D sterols, which may elevate calcium and/or phosphorus levels. Such elevation would frequently require treatment to be interrupted and lead to an inadequate control of PTH.

It is now well-accepted that Sensipar® provides an excellent targeted treatment of secondary HPT with its unique mechanism of action that acts directly on the calcium-sensing receptor. Sensipar® provides significant improvement over traditional therapy to provide an important new tool to help dialysis patients suffering from secondary HPT. It also is successful in lowering calcium levels in patients with hypercalcemia due to parathyroid carcinoma. Patients with parathyroid carcinoma have a rare, serious cancer of the parathyroid gland results in excess secretion of PTH. Thus, parathyroid carcinoma is one form of primary HPT. The disease is complicated by elevated calcium levels in the blood. High calcium levels can lead to anxiety, depression, nausea, vomiting, bone fractures, kidney stones and in some cases coma. Surgical removal of the parathyroid gland is the only curative therapy for this disease but is not successful in all cases. Sensipar® was shown to reduce high levels of calcium in patients with parathyroid carcinoma.

A need exists for synthetic processes for cinacalcet, cinacalcet derivatives, and salts thereof.

SUMMARY

The present disclosure is directed to processes and intermediates for the synthesis of cinacalcet, cinacalcet derivatives, and salts thereof. In various embodiments, a cinacalcet salt is prepared. In a specific class of embodiments, cinacalcet hydrochloride is prepared.

Thus, one aspect of the invention provides a method of preparing cinacalcet using allylic amination. The method comprises (a) admixing a compound of formula (I) and a compound of formula (II) under conditions that permit cross-metathesis to produce a compound of formula (III):

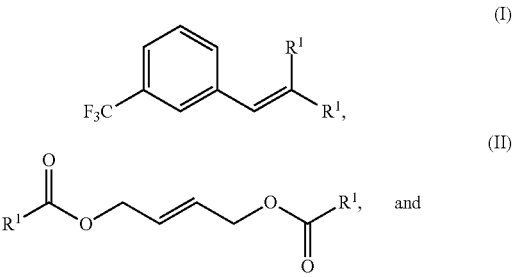

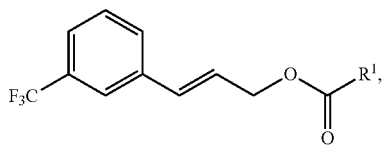
(III)

wherein each R¹ is the same or different and is selected from the group consisting of hydrogen, $C_1$-$C_6$ alkyl, $OC_1$-$C_6$ alkyl, aryl, O-aryl, heteroaryl, and O-heteroaryl; b) admixing compound (III) and 1-(1-naphthyl)ethylamine or a salt thereof under conditions to permit allylic amination to produce a compound of formula (IV)

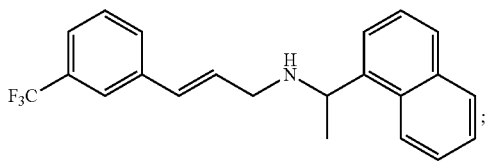
(IV)

and c) reducing compound (IV) under conditions that permit reduction to produce cinacalcet or a salt thereof. In various embodiments, the conditions that permit cross-metathesis can include performing said cross-metathesis in the presence of a Ru or Mo catalyst. In various embodiments, the conditions that permit allylic amination can include performing said allylic amination in the presence of a Pd, Ru, Ir, Rh, Pt, or Ni catalyst. In various embodiments, the conditions that permit reduction can include performing said reduction in the presence of a reducing agent (e.g., hydrogen, hydride, or the like) and a Pd, Ni, Pt, Rh, Ir, or Ru catalyst.

In another aspect, a method of preparing cinacalcet or salt thereof comprises a) admixing a compound of formula (V) and 1-(1-naphthyl)ethylamine under conditions to permit allylic amination to produce a compound of formulation (IV):

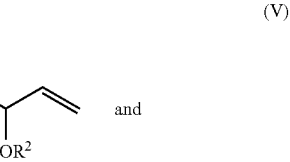
(V)

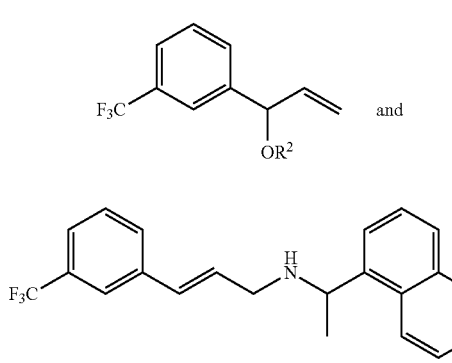
(IV)

wherein R² is selected from the group consisting of hydrogen, $C_1$-$C_6$ alkyl, aryl, heteroaryl, $C(O)C_1$-$C_6$ alkyl, C(O)aryl, C(O)heteroaryl, and $C(O)OC_1$-$C_6$ alkyl; and b) reducing compound (IV) under conditions that permit reduction to produce cinacalcet or a salt thereof. In various embodiments, the conditions that permit allylic amination can include performing said allylic amination in the presence of a Pd catalyst. In various embodiments, the conditions that permit reduction can include performing said reduction in the presence of a reducing agent (e.g., hydrogen, hydride, or the like) and a Pd, Ni, Pt, Rh, Ru, or Ir catalyst. In various embodiments, the compound of formula (V) can be prepared via a method comprising admixing 3-trifluoromethyl-benzaldehyde and a vinyl reagent to form a compound of formula (V). In specific embodiments, the vinyl reagent is vinyl lithium, vinyl borate, vinyl boronate, vinyl zinc halide, divinyl zinc, or vinyl magnesium halide.

In another aspect, a method of preparing cinacalcet or salt thereof comprises a) admixing a compound of formula (V), where R² is hydrogen, and 1-(1-naphthyl)ethyl isocyanate under conditions that permit the formation of a compound of formula (VI):

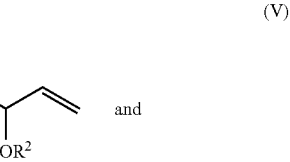
(V)

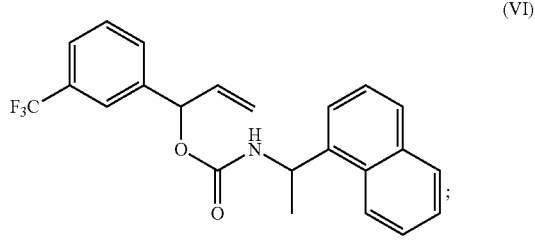
(VI)

b) admixing compound (VI) and a catalyst under conditions that permit C—O to C—N rearrangement to form a compound of formula (IV)

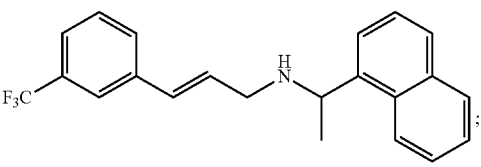
(IV)

and c) reducing compound (IV) under conditions that permit reduction to produce cinacalcet or a salt thereof. In various embodiments, the conditions which permit C—O to C—N rearrangement can include performing said C—O to C—N rearrangement in the presence of a metal catalyst, wherein the metal catalyst is selected from the group consisting of Pd, Ru, Ni, Ir, Rh, Hg, Au, and Pt. In various embodiments, the conditions that permit reduction can include performing said reduction in the presence of a reducing agent (e.g., hydrogen, hydride, or the like) and a Pd, Ni, Ir, Pt, Rh, Ru or Ir catalyst.

In another aspect, a method of preparing cinacalcet or salt thereof comprises a) admixing 3-trifluoromethyl-cinnamic acid and 1-(1-naphthyl)ethylamine under conditions to permit amide bond formation to form a compound of formula (VIIB)

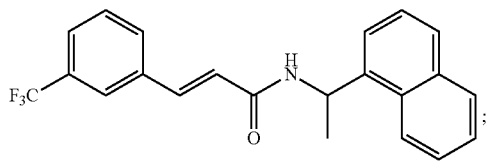

and b) reducing compound (VIIB) under conditions that permit reduction to form cinacalcet or a salt thereof. In various embodiments, the conditions that permit amide bond formation can include performing said amide bond formation in the presence of a peptide coupling agent. In specific embodiments, the peptide coupling agent can be a chlorinating agent (e.g., oxalyl chloride, thionyl chloride, or phosphorus trichloride), a mixed anhydride, DIC, DCC, EDCI, CDI, HOBt, HOAt, pentafluorophenol, HBTU, HATU, and Mukaiyama's reagent. In various embodiments, the conditions that permit reduction can include performing said reduction in the presence of a reducing agent (e.g., hydrogen, hydride, or the like) and a Pd, Ni, Ir, Pt, Rh, Ru or Ir catalyst. In various embodiments, the reduction can be in the presence of borane or lithium aluminum hydride. In certain embodiments, the reduction conditions are sufficient to reduce both the double bond and the amide bond, while in certain other embodiments, two different reduction conditions are used to reduce the double bond and the amide bond, in either order.

In still another aspect, a method of preparing cinacalcet or salt thereof comprises a) admixing a compound of formula (VIII) and a compound of formula (IX), under conditions that promote coupling of compound (VIII) and compound (IX) to form compound (X)

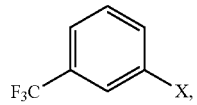

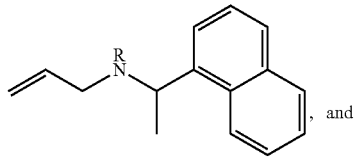

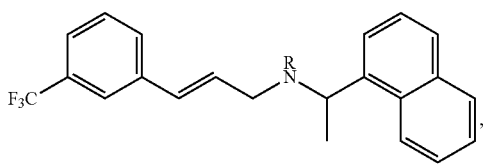

wherein X is selected from the group consisting of chlorine, bromine, iodine, $OSO_2C_6H_4CH_3$, $OSO_2CH_3$, $OSO_2CF_3$, $OSO_2C_4F_9$ and $N_2^+$ and R is selected from the group consisting of hydrogen, benzyl, substituted benzyl, BOC, CBZ, and acetate; and b) reducing compound (XI) under conditions that permit reduction to form cinacalcet, a cinacalcet derivative, or a salt thereof. In various embodiments, the conditions that promote coupling of compound (VIII) and compound (IX) can include performing said coupling in the presence of a Pd or Ni catalyst. In various embodiments, the conditions that permit reduction can include performing said reduction in the presence of a reducing agent (e.g., hydrogen, hydride, or the like) and a Pd, Ni, Ir, Pt, Rh, Ru or Ir catalyst. In embodiments where R is not hydrogen, the method optionally further includes deprotecting the cinacalcet derivative to form cinacalcet or a salt thereof.

In yet another aspect, a method of preparing cinacalcet, a derivative thereof, or salt thereof comprises a) admixing a compound of formula (VIII) and a compound of formula (XI), under conditions that promote coupling of compound (VIII) and compound (XI) to form compound (XII)

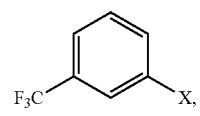

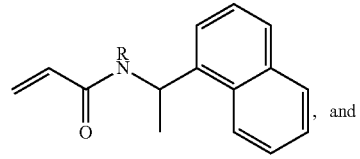

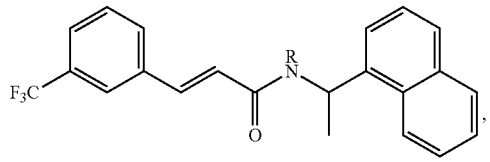

wherein X is selected from the group consisting of chlorine, bromine, iodine, $OSO_2C_6H_4CH_3$, $OSO_2CH_3$, $OSO_2CF_3$, $OSO_2C_4F_9$, and $N_2^+$ and R is selected from the group consisting of hydrogen, benzyl, BOC, CBZ, and acetate; b) reducing compound (XII) under conditions that permit reduction to form cinacalcet, a cinacalcet derivative, or a salt thereof. In various embodiments, the conditions that promote coupling of compound (VIII) and compound (XI) can include performing said coupling in the presence of a Pd catalyst or a Ru catalyst. In various embodiments, the conditions that permit reduction can include performing said reduction in the presence of a reducing agent (e.g., hydrogen, hydride, or the like) and a Pd, Ni, Ir, Pt, Rh, Ru or Ir catalyst. In embodiments where R is not hydrogen, the method optionally further includes deprotecting the cinacalcet derivative to form cinacalcet or a salt thereof.

In still another aspect, a method of preparing cinacalcet or salt thereof comprises reducing a compound of formula (XIII) under conditions that permit reduction to form cinacalcet or a salt thereof

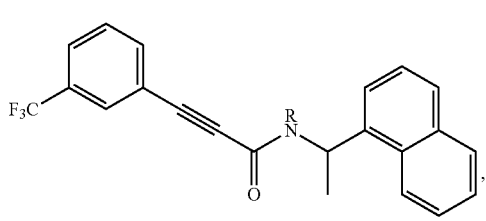

wherein R is selected from the group consisting of hydrogen, benzyl, substituted benzyl, BOC, Cbz, and acetate. In various embodiments, the method further can include (i) admixing a compound of formula (VIII) and propiolic acid or an ester thereof under conditions that permit coupling of compound (VIII) and propiolic acid or an ester thereof to form a compound of formula (XIV)

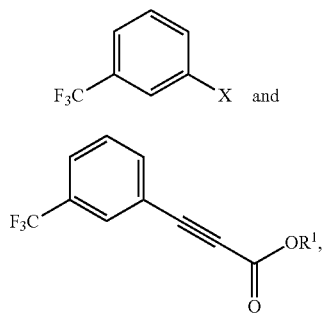

(VIII)

(XIV)

wherein X is selected from the group consisting of chlorine, bromine, iodine, $OSO_2C_6H_4CH_3$, $OSO_2CH_3$, $OSO_2CF_3$, $OSO_2C_4F_9$, and $N_2^+$ and $R^1$ is selected from the group consisting of hydrogen, $C_1$-$C_6$ alkyl, and aryl; and (ii) admixing compound (XIV) and 1-(1-naphthyl)ethylamine or a salt thereof under conditions that permit amide bond formation to form the compound of formula (XIII). In a specific class of embodiments, the conditions that permit coupling of compound (VIII) and propiolic acid or an ester thereof can include performing said coupling in the presence of a Pd catalyst. In various embodiments, the method further comprises admixing a compound of formula (VIII) and a compound of formula (XV) under conditions that permit coupling of a compound of formula (VIII) and a compound of formula (XV) to form the compound of formula (XIII)

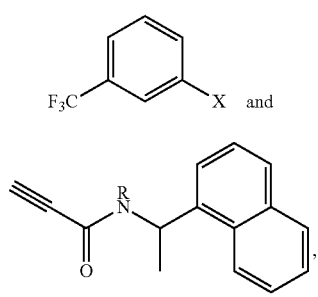

(VIII)

(XV)

wherein X is selected from the group consisting of chlorine, bromine, iodine, $OSO_2C_6H_4CH_3$, $OSO_2CH_3$, $OSO_2CF_3$, $OSO_2C_4F_9$, and $N_2^+$. In a specific class of embodiments, the conditions that permit coupling of the compound of formula (VIII) and the compound of formula (XV) can include performing said coupling in the presence of a Pd catalyst. In various embodiments, the method includes admixing 3-trifluoromethyl-phenylacetylene and 1-(1-naphthyl)ethyl isocyanate under conditions that permit the coupling of 3-trifluoromethyl-phenylacetylene and 1-(1-naphthyl)ethyl isocyanate to form the compound of formula (XIII), wherein R is H. In a specific class of embodiments, the conditions that permit coupling of 3-trifluoromethyl-phenylacetylene and 1-(1-naphthyl)ethyl isocyanate can include performing said coupling in the presence of a base. In embodiments where R is not H, the method optionally further includes deprotecting the cinacalcet derivative to form cinacalcet or a salt thereof.

In another aspect, a method of preparing cinacalcet, a derivative thereof, or salt thereof comprises reducing a compound of formula (XVI) under conditions that permit reduction to form cinacalcet, a cinacalcet derivative, or a salt thereof

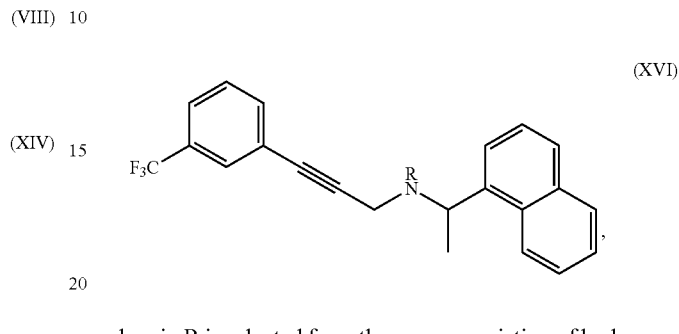

(XVI)

wherein R is selected from the group consisting of hydrogen, benzyl, substituted benzyl, BOC, Cbz, and acetate. In various embodiments, the method further comprises admixing a compound of formula (VIII) and a compound of formula (XVII) under conditions that permit coupling of compound (VIII) and compound (XVII) to form compound (XVI),

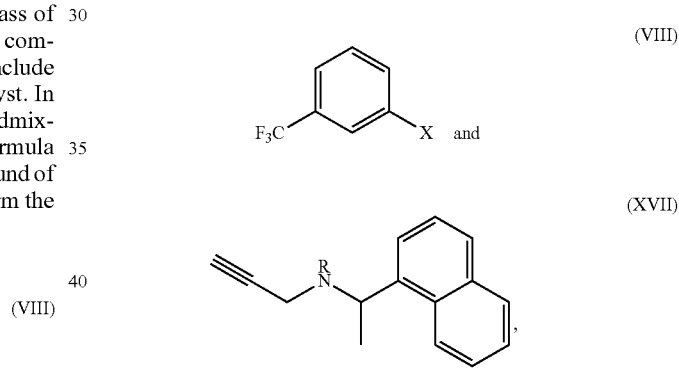

(VIII)

(XVII)

wherein X is selected from the group consisting of chlorine, bromine, iodine, $OSO_2C_6H_4CH_3$, $OSO_2CH_3$, $OSO_2CF_3$, $OSO_2C_4F_9$, and $N_2^+$. In a specific class of embodiments, the conditions that permit coupling of formula (VIII) and formula (XVII) can include performing said coupling in the presence of a Pd catalyst. In embodiments where R is not hydrogen, the method optionally further includes deprotecting the cinacalcet derivative to form cinacalcet or a salt thereof.

In yet another aspect, a method of preparing cinacalcet or salt thereof comprises a) admixing a compound of formula (I) and a compound of formula (XVIII) under conditions that permit cross-metathesis to produce a compound of formula (IV):

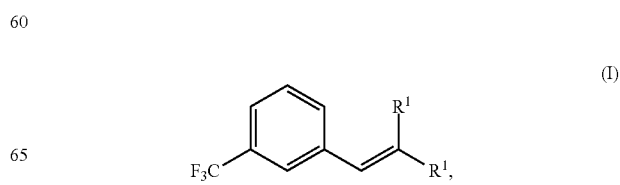

(I)

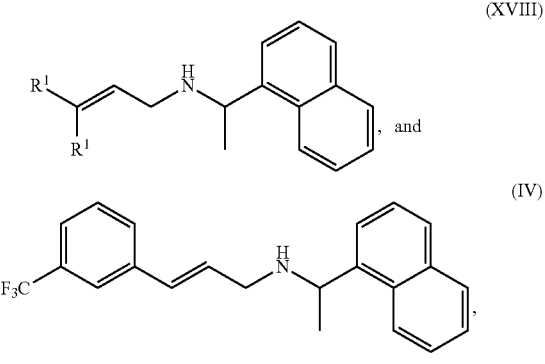

(XVIII)

(IV)

wherein each $R^1$ is the same or different and is selected from the group consisting of hydrogen and $C_1$-$C_6$ alkyl; and b) reducing compound (IV) under conditions that permit reduction to produce cinacalcet or a salt thereof. In various embodiments, the conditions that permit cross-metathesis can include performing said cross-metathesis in the presence of a Ru catalyst. In various embodiments, each $R^1$ is selected from hydrogen and methyl. In various embodiments, the conditions that permit reduction in step (b) can include performing said reduction in the presence of a reducing agent (e.g., hydrogen, hydride, or the like) and a Pd, Ni, Ir, Pt, Rh, Ru or Ir catalyst.

In still another aspect, a method of preparing cinacalcet or salt thereof comprises a) admixing a compound of formula (I) and a compound of formula (XIX) under conditions that permit cross-metathesis to produce a compound of formula (VIIB):

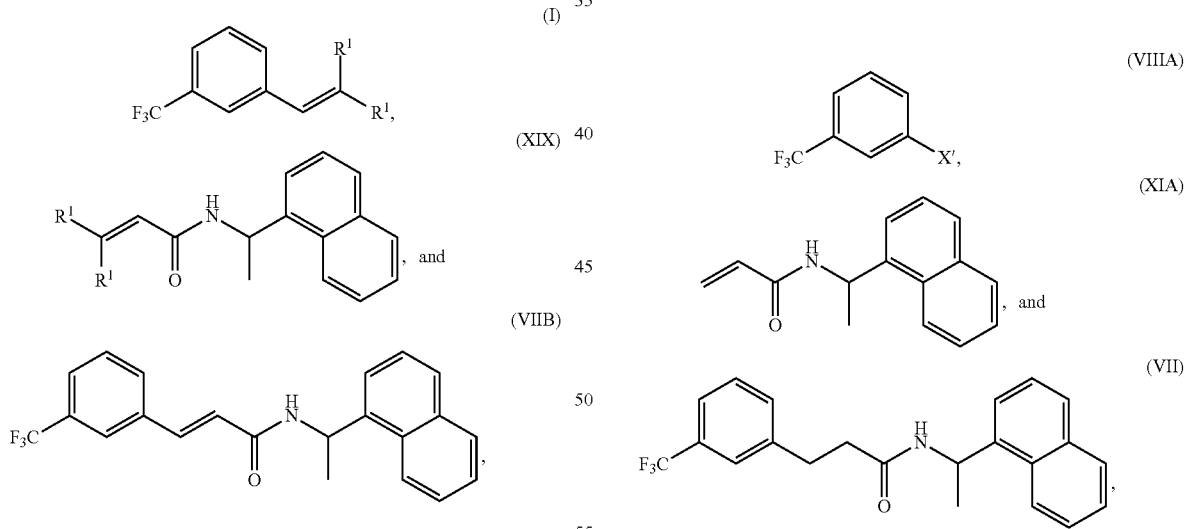

(I)

(XIX)

(VIIB)

wherein each $R^1$ is the same or different and is selected from the group consisting of hydrogen and $C_1$-$C_6$ alkyl; and b) reducing compound (VIIB) under conditions that permit reduction to produce cinacalcet or a salt thereof. In various embodiments, the conditions that permit cross-metathesis can include performing said cross-metathesis in the presence of a Ru catalyst. In various embodiments, each $R^1$ is selected from hydrogen and methyl. In various embodiments, the conditions that permit reduction in step (b) can include performing said reduction in the presence of a reducing agent (e.g., hydrogen, hydride, or the like) and a Pd, Ni, Ir, Pt, Rh, Ru or Ir catalyst.

In another aspect, a method of preparing cinacalcet or salt thereof comprises a) admixing 3-(trifluoromethyl)styrene, carbon monoxide, and hydrogen, under conditions that permit hydroformylation to produce 3-(3-trifluoromethylphenyl)propanal; b) admixing 3-(3-trifluoromethylphenyl)propanal and 1-(1-naphthyl)ethylamine under conditions that permit imine formation to form a compound of formula (XX)

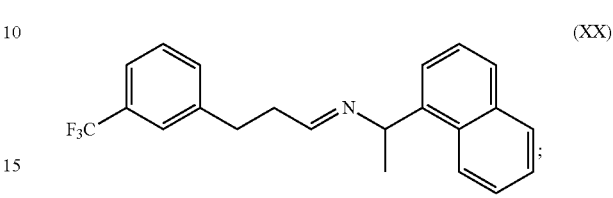

(XX)

and c) reducing the compound of formula (XX) under conditions that permit reduction to produce cinacalcet or a salt thereof. In various embodiments, the conditions to permit hydroformylation can include performing said hydroformylation in the presence of a Rh, Co, or Pt catalyst. In various embodiments, the conditions that permit imine formation can include performing said imine formation in the presence of an acid. In various embodiments, the conditions to permit reduction can include performing said reduction in the presence of a reducing agent (e.g., hydrogen, hydride, or the like) and a Pd, Ni, Ir, Pt, Rh, Ru or Ir catalyst or in the presence of a hydride source, such as lithium aluminum hydride.

In another aspect, a method of preparing cinacalcet or a salt thereof comprises a) admixing a compound of formula (VIIIA) and a compound of formula (XIA), under conditions that promote the coupling of compound (VIIIA) and compound (XIA) to form a compound of formula (VII):

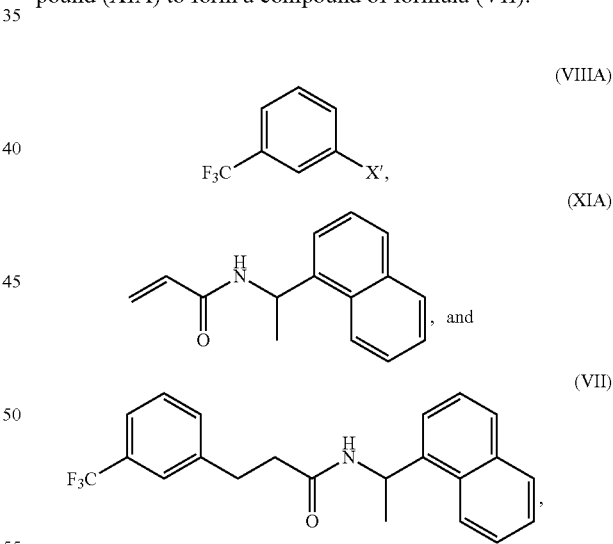

(VIIIA)

(XIA)

(VII)

wherein X' is selected from the group consisting of $B(OH)_2$, $Si(OR^3)_3$, $Sn(R^3)_3$, and $Ti(OR^3)_3$, and $R^3$ is the same or different and is independently selected from the group consisting of hydrogen and $C_{1-6}$alkyl; and b) reducing compound (VII) under conditions that permit reduction to form cinacalcet or a salt thereof. In various embodiments, the conditions that promote the coupling of compound (VIIIA) and compound (XIA) can include performing the coupling in the presence of a Rh or Pd catalyst. In various embodiments, the conditions that permit reduction can include performing said reduction in the presence of a reducing agent. In a specific class of embodiments, the reducing agent can comprise sodium borohydride (NaBH$_4$), lithium borohydride (LiBH$_4$), calcium borohydride (Ca(BH$_4$)$_2$), lithium aluminum hydride (LiAlH$_4$) or complexes of BH$_3$ with THF, Et$_3$N or Me$_2$S.

In still another aspect, a method of preparing cinacalcet or salt thereof comprises admixing 3-(trifluoromethyl)styrene, carbon monoxide, hydrogen and 1-(1-naphthyl)ethylamine, under conditions that permit hydroformylation, imine formation, and reduction (hydroaminomethylation) to produce cinacalcet or a salt thereof. In various embodiments, the conditions that permit hydroformylation, imine formation, and reduction can include performing said hydroformylation, said imine formation, and said reduction in the presence of a Rh or Co catalyst.

In yet another aspect, a method of preparing cinacalcet or salt thereof comprises admixing 1-(3-trifluoromethylphenyl)-2-propene, borane, and N-chloro-1-(1-naphthyl)ethylamine under conditions that permit hydroboration and C—N coupling to form cinacalcet or a salt thereof. In various embodiments, the conditions to permit reduction can include performing said reduction in the presence of a base.

In a specific class of embodiments, the processes disclosed herein can provide cinacalcet hydrochloride. In various embodiments, the processes disclosed herein can provide cinacalcet hydrochloride having a powder X ray powder diffraction (XRPD) pattern having peaks at diffraction angle 2θ of about 16.6942; 17.6152; 19.4992; 20.2946; and 20.5877. In various embodiments, the XRPD pattern may further comprise at least one diffraction angle 2θ peak selected from the group consisting of 12.3402; 14.4334; 15.3545; 16.443; 18.2013; 18.6618; 19.9178; 21.7599; 21.9692; 22.4297; 24.0206; and 25.0672. In various other embodiments, the crystalline polymorph of the invention has an XRPD pattern comprises at least diffraction angle 2 θ peaks at about 12.3402; 14.4334; 15.3545; 16.443; 16.6942; 17.6152; 18.2013; 18.6618; 19.4992; 19.9178; 20.2946; 20.5877; 21.7599; 21.9692; 22.4297; 24.0206; and 25.0672. In still other embodiments, the crystalline polymorph has an XRPD pattern comprises diffraction angle 2 θ peaks at about 12.3402; 14.4334; 15.3545; 16.443; 16.6942; 17.6152; 18.2013; 18.6618; 19.4992; 19.9178; 20.2946; 20.5877; 21.7599; 21.9692; 22.4297; 24.0206; and 25.0672. In a specific embodiment, the cinacalcet hydrochloride produced via the disclosed methods is polymorph III.

In another aspect, compositions of cinacalcet hydrochloride prepared via any of the disclosed methods are disclosed. The compositions can include the cinacalcet hydrochloride and a pharmaceutically acceptable carrier.

In yet another aspect, methods of treating a subject suffering from hypercalcemia comprising administering to said subject a composition as disclosed herein, wherein the composition comprises a therapeutically effective amount of cinacalcet or salt thereof.

DETAILED DESCRIPTION

Disclosed herein are synthetic processes for the preparation of cinacalcet, cinacalcet derivatives, or salts thereof, collectively referred to as "cinacalcet" throughout this disclosure.

The compounds, intermediates, and polymorphs disclosed herein can be in an isolated or purified form. Such forms include those that are at least about 80% pure by weight, as measured by an analytical process, such as one or more of liquid chromatography, elemental analysis, mass spectrometry, nuclear magnetic resonance, gas chromatography, and the like. Other isolated or purified forms can include at least about 85%, at least about 90%, at least about 91%, at least about 92%, at least about 93%, at least about 94%, at least about 95%, at least about 96%, at least about 97%, at least about 98%, and at least about 99%.

The various synthetic processes are discussed in detail below.

Allylic Amination Routes

Cinacalcet can be prepared using an allylic amination, via two synthetic pathways. In one pathway, a 3-trifluoromethylstyrene derivative (a compound of formula (I)) reacts with a 2-butendiol ester derivative (a compound of formula (II)) under cross metathesis conditions to form a compound of formula (III). (See Scheme 1, step (1a)). The intermediate compound of formula (III) then undergo allylic amination with 1-(1-naphthyl)ethylamine to provide a compound of formula (IV) (Scheme 1, step (1b)). Compound (IV) can then be reduced under the appropriate conditions to form cinacalcet or a salt thereof (Scheme 1, step (1c)).

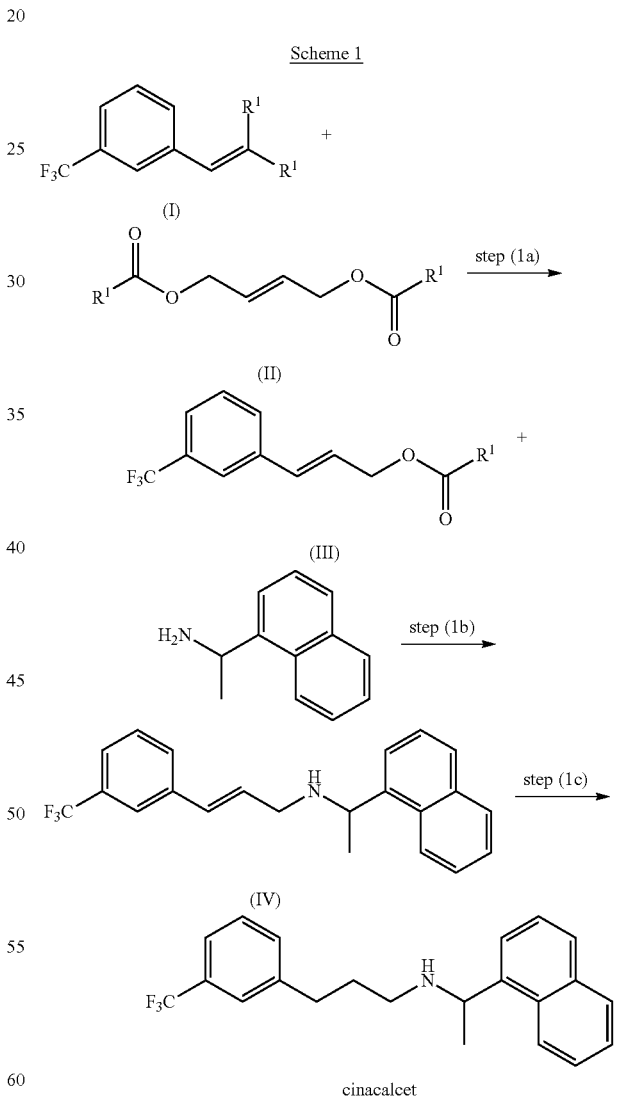

For compounds of formulae (I), (II), and (III), R$^1$ can be independently hydrogen, C$_1$-C$_6$ alkyl, OC$_1$-C$_6$ alkyl, aryl, O-aryl, heteroaryl, or O-heteroaryl. In various embodiments, the compound of formula (III) has a R$^1$ of C$_{1-6}$alkyl when subjected to the conditions of step (1b).

As used herein, the term "alkyl" refers to straight chained and branched hydrocarbon groups, nonlimiting examples of which include methyl, ethyl, and straight chain and branched propyl and butyl groups.

As used herein, the term "aryl" refers to a monocyclic or polycyclic aromatic group, preferably a monocyclic or bicyclic aromatic group, e.g., phenyl or naphthyl. Unless otherwise indicated, an aryl group can be unsubstituted or substituted with one or more, and in particular one to four groups independently selected from, for example, halo, alkyl, alkenyl, $OCF_3$, NO2, CN, NC, OH, alkoxy, amino, $CO_2H$, $CO_2$alkyl, aryl, and heteroaryl. Exemplary aryl groups include, but are not limited to, phenyl, naphthyl, tetrahydronaphthyl, chlorophenyl, methylphenyl, methoxyphenyl, trifluoromethylphenyl, nitrophenyl, 2,4-methoxychlorophenyl, and the like.

As used herein, the term "heteroaryl" refers to a monocyclic or bicyclic ring system containing one or two aromatic rings and containing at least one nitrogen, oxygen, or sulfur atom in an aromatic ring. Unless otherwise indicated, a heteroaryl group can be unsubstituted or substituted with one or more, and preferably one to four, substituents selected from, for example, halo, alkyl, alkenyl, $OCF_3$, $NO_2$, CN, NC, OH, alkoxy, amino, $CO_2H$, $CO_2$alkyl, aryl, and heteroaryl. Examples of heteroaryl groups include, but are not limited to, thienyl, furyl, pyridyl, oxazolyl, quinolyl, thiophenyl, isoquinolyl, indolyl, triazinyl, triazolyl, isothiazolyl, isoxazolyl, imidazolyl, benzothiazolyl, pyrazinyl, pyrimidinyl, thiazolyl, and thiadiazolyl.

The conditions that permit cross metathesis (step (1a)) include using ruthenium and molybdenum based complexes capable of catalyzing olefin metathesis. Cross metathesis catalysts include, but are not limited to, Grubbs' catalyst and Schrock's catalyst. Specific catalysts contemplated include [1,3-bis(2,4,6-trimethylphenyl)-2-imidazolidinylidene] dichloro (phenylmethylene) (tricyclohexylphosphine) ruthenium and [1,3-bis(2,4,6-trimethylphenyl)-2-imidazolidinylidene]dichloro[[2-(1-methylethoxy)phenyl]methylene ruthenium. Other catalysts that can be used in the methods disclosed herein included those described in U.S. Pat. Nos. 5,110,948; 5,342,909; 6,313,365; 6,316,380; 6,362,357; 6,369,265; 6,403,801; 6,403,802; 6,417,363; 6,426,419; 6,500,975; 6,583,307; 6,586,599; 6,610,626; 6,613,910; 6,620,955; 6,635,768; 6,800,170; 6,803,429; 6,818,586; 6,844,442; 6,867,303; 6,900,347; 7,026,495; and 7,205,424.

Conditions that permit allylic amination (step (1b)) include reaction in the presence of a transition metal catalyst. Specific catalysts contemplated include Pd-phosphine complexes such as, but not limited to, tetrakis(triphenylphosphine)palladium. The transition metal of the transition metal catalyst used in allylic amination is typically Ni, Mo, Pt, Co, Ru, Rh, Ir, Mn, V, Cr, Ag, Fe, Cu or Pd. The ligands of the transition metal catalyst contain a coordinating atom, through which the ligand coordinates to the transition metal. The coordinating atom typically is N, P or S, and possibly O or C. Examples of ligands include, but are not limited to, cyclooctadiene, cycloheptatriene, CO, $C_7H_8$, and Cl. Examples of transition metal catalysts include, but are not limited to, Pd catalysts, $Ni(COD)_2$, $Mo(CO)_3(C_7H_8)$, $Pt(PPh_3)_4$, $RhCl(PPh_3)_2$, and $CoCl_2$. Pd catalysts are generally preferred transition metal catalysts for use in the allylic amination reaction. Examples of suitable nitrogen protecting groups for the allylic amination include, but are not limited to, $C_6H_2$-3,4,5-$(OMe)_3$, benzhydryl, PNP (p-nitrophenyl), Boc, and PMP (p-methoxyphenyl). Other suitable nitrogen protecting groups can be found in Wuts et al., *Greene's Protective Groups in Organic Synthesis*, 4$^{th}$ ed., (Wiley Interscience: Hoboken, N.J.) 2007.

Suitable organic solvents for the allylic amination include, but are not limited to, hexane, tetrahydrofuran, acetonitrile, dichloromethane, chlorobenzene, dichloroethane, toluene, ethyl acetate, methyl t-butyl ether, diethyl ether, or mixtures thereof. The allylic amination reaction may also optionally be performed in the presence of a base. Examples of suitable bases include, but are not limited to, triethylamine and diisopropylethylamine.

Other conditions which permit allylic amination include those disclosed in the following Patent or Patent Publications: U.S. Pat. No. 7,173,157; U.S. Pat. No. 7,071,357; WO 2002/040491; and US 20060199728.

Conditions that permit reduction of the double bond (e.g., step (1c)) include hydrogenation using hydrogen source and, optionally, a catalyst. Catalytic reduction can be carried out in a polar solvent, for example in an alcohol such as methanol, ethanol, propanol and in water and an organic acid, such as acetic acid, or mixture thereof. Catalysts used in reduction reaction under a hydrogen atmosphere are, for instance, palladium, platinum, Raney nickel, and the like. The hydrogen source is typically hydrogen gas, but can be some other reagent that permits reduction of a double bond to a single bond.

In a second pathway for the synthesis of cinacalcet via allylic amination, a compound of formula (V) undergoes allylic amination to form a compound of formula (IV) trifluoromethylbenzaldehyde is reacted with a vinyl reagent, prior to allylic amination and reduction, as depicted in Scheme 2, below. Steps (2b) and (2c) can occur as described above for steps (1b) and (1c).

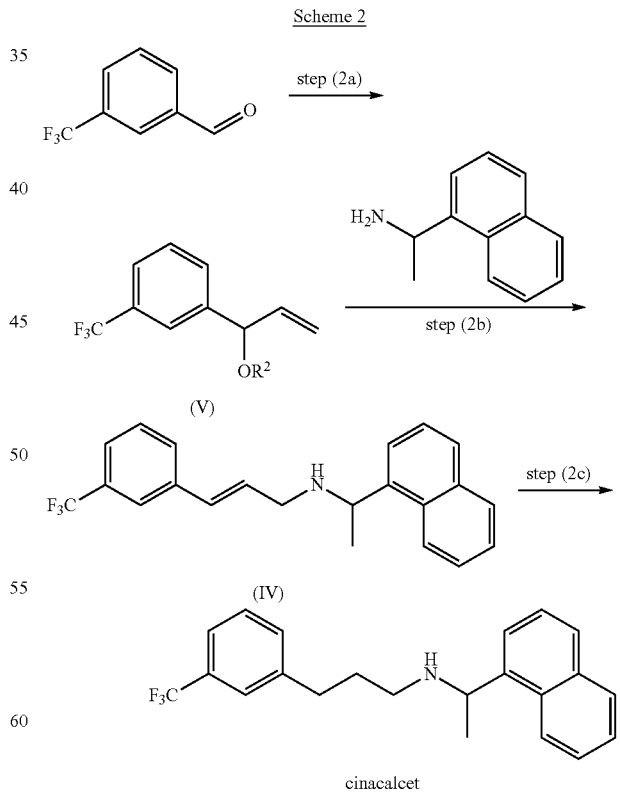

Scheme 2

In various embodiments of the methods described herein, the compound of formula (V) is prepared by admixing 3-trifluoromethylbenzaldehyde and a vinyl nucleophile reagent (step (2a)) and optionally modifying the resulting vinyl alcohol to an ether, ester, or carbonate using known techniques, such that $R^2$ can be $C_{1-6}$alkyl, $C(O)C_{1-6}$alkyl, $C(O)OC_{1-6}$alkyl, or $C(O)OC_{1-6}$alkylenearyl. In specific embodiments, $R^2$ can be hydrogen, acetate, Boc, or $CO_2$Me. The conditions that permit nucleophilic attack by the vinyl reagent are typically anhydrous. In one specific embodiment, vinyl lithium is admixed with 3-trifluoromethylbenzaldehyde to form a compound of formula (V), wherein $R^2$ is hydrogen. Alternatively, compound (V) can be prepared by admixing vinyl chloride with magnesium metal (optionally in the presence of iodine) to form vinyl magnesium chloride, which is then admixed with 3-trifluoromethylbenzaldehyde to form a compound of formula (V), wherein $R^2$ is hydrogen. This intermediate is then optionally modified to give a compound of formula (V) wherein $R^2$ is acetate, Boc, or $CO_2$Me, prior to subjecting the compound of formula (V) to allylic amination conditions.

C—O to C—N Rearrangement

Cinacalcet can alternatively be prepared using a C—O to C—N rearrangement. In this synthetic approach, as outlined in Scheme 3, a compound of formula (V), wherein $R^2$ is hydrogen is admixed with a reagent, such as 1-(1-naphthyl)ethyl isocyanate or a 1-(1-naphthyl)ethyl carbamoyl chloride, under appropriate conditions to form a compound of formula (VI) (step 3a). The compound of formula (VI) can then be admixed with a catalyst under conditions that permit C—O to C—N rearrangement to form a compound of formula (IV) (step 3b). The compound of formula (IV) can subsequently undergo hydrogenation to form cinacalcet (step (3c)), as described above for step (1c).

The conditions that permit formation of a compound of formula (VI) (step (3a)) can include admixture in the presence of a metal catalyst, such as described in Kim et al, Synlett, 3:261-262 (1998). In various embodiments, step (3a) occurs in the presence of a base, such as metal alkoxides, alkyl lithiums, metal hydroxides, and the like.

The conditions that permit C—O to C—N rearrangement include contacting the compound of formula (VI) with a metal catalyst that facilitates C—O to C—N rearrangements. Such metal catalysts include Pd, Ru, Ni, Hg, Au, Ir, Rh, and Pt (see Mellegaard-Waetzig, et al., Synlett, 18:2759-2762 (2005)). Specific conditions contemplated for the C—O to C—N rearrangement include reaction in the presence of tetrakis(triphenylphosphine)palladium or (pentamethylcyclopentadienyl)ruthenium chloride tetramer.

Peptide Coupling

Cinacalcet can alternatively be prepared using peptide coupling methods. Such a synthetic route is outlined, below, in Scheme 4, starting from 3-trifluoromethylcinnamic acid or a 3-trifluoromethyl dihydrocinnamic acid.

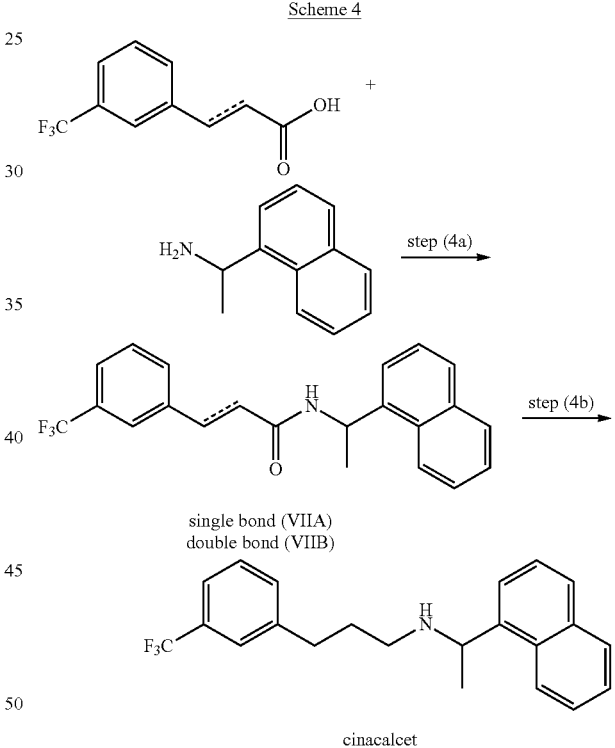

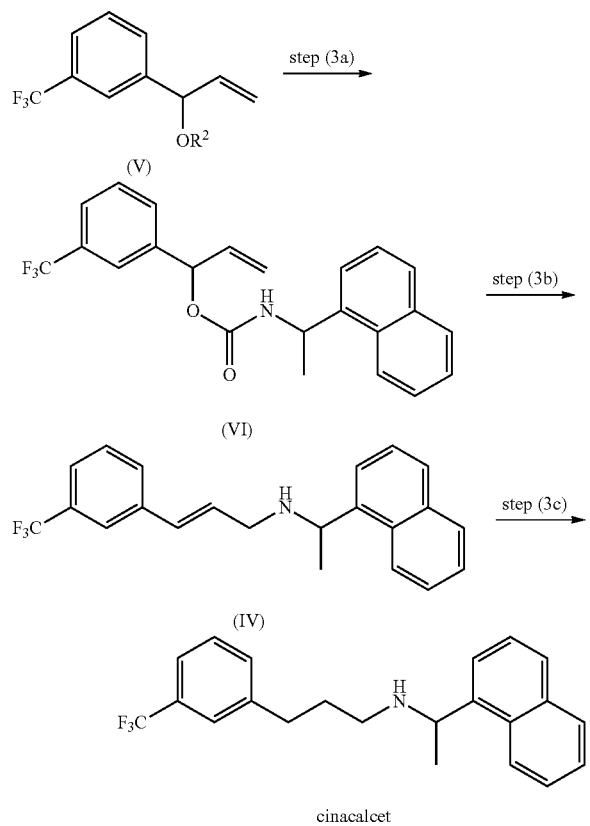

Peptide coupling (e.g., step (4a)) can occur under a variety of conditions. Typically admixture of an acid or activated acid and an amine occurs in a compatible organic solvent, such as methylene chloride, THF, DMF, DMSO, ethyl acetate, or the like. Coupling reagents that facilitate the formation of an amide bond between an amine and a carboxylic acid can be employed. Preferred coupling agents include DCC, DIC, O-benzotriazolyl-1-yl-1,1,3,3-tetramethyluronium hexafluorophosphate(HBTU), O-(7-azabenzotriazol-1-yl-1,1,3,3-tetramethyluronium hexafluorophosphate (HATU); O-(7-azabenzotriazol-1-yl-1,1,3,3-bis (tetramethylene uronium hexafluorphosphate (HApyU), O-(7-azabenzotriazol-1-yl)-1,1,3,3-bis(pentamethylene)uronium hexafluorophosphate (HApipU), O-(7-azabenzotrizol-1-yl)-1,3-dimethyl-1, 3-trimethylene uronium hexafluorophosphate (HAMTU), benzotriazolyl-yl-1,1,3,3-bis(tetramethylene uronium tetrafluoroborate) (TBTU), TFFH, or reagents that form in situ acid chlorides, mixed anhydrides, EZDQ, active esters, such as pentafluorophenyl or succinimide esters of the carboxylic acid.

For reduction of a compound of formula (VIIB) to cinacalcet, reduction of the double bond and of the carbonyl to a methylene moiety can occur simultaneously or serially under the same conditions or separate conditions. In various embodiments, the partially reduced intermediate—such as reduction of the double bond first to form an intermediate compound of formula (VIIA) or reduction of the carbonyl first to form a compound of formula (IV)—is isolated prior to the subsequent reduction to form cinacalcet, while in other embodiments, the partially reduced intermediate is subsequently fully reduced to form cinacalcet without isolation and/or purification. Reduction of a carbonyl to a methylene moiety can be achieved by admixing the compound of formula (VIIB) or formula (VIIA) with a reducing agent. Reducing agents include, but are not limited to, metal hydrides such as sodium borohydride (NaBH$_4$), lithium borohydride (LiBH$_4$), calcium borohydride (Ca(BH$_4$)$_2$), lithium aluminum hydride (LiAlH$_4$) or complexes of BH$_3$ with THF, Et$_3$N or Me$_2$S. The reduction of the double bond of the compound of formula (VII) can occur under the conditions described above, for step (1c).

Heck Couplings

Cinacalcet can be prepared by coupling of an aryl halide with an appropriate corresponding compound. Heck, Sonagashira, Suzuki, Hiyama, and Stille couplings are all contemplated as synthetic routes for the preparation of cinacalcet. For Heck coupling, a compound of formula (VIII) is reacted with an allyl amine compound of formula (IX) or an acrylamide compound of formula (XI) under conditions that permit coupling of the two compounds, to form a compound of formula (X) or a compound of formula (XII), respectively, as shown in Scheme 5. For compounds of formula (VIII), X can be a halogen (e.g., F, Cl, Br, or I), or can be a triflate (OSO$_2$CF$_3$), tosyl (OSO$_2$C$_6$H$_4$CH$_3$), mesyl (OSO$_2$CH$_3$), nonaflate (OSO$_2$C$_4$F$_9$) or any other functional group that is compatible with a Heck, Sonagashira, Suzuki, Hiyama, or Stille coupling.

Scheme 5

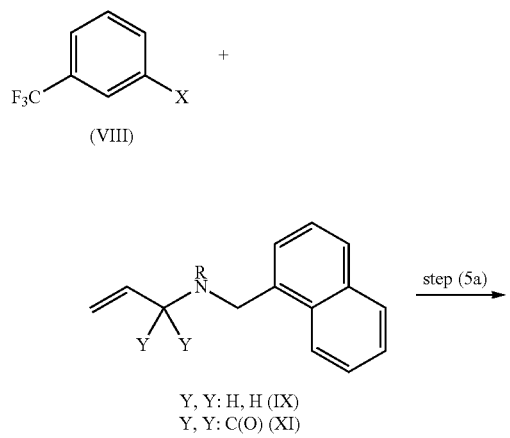

Y, Y: H, H (IX)
Y, Y: C(O) (XI)

-continued

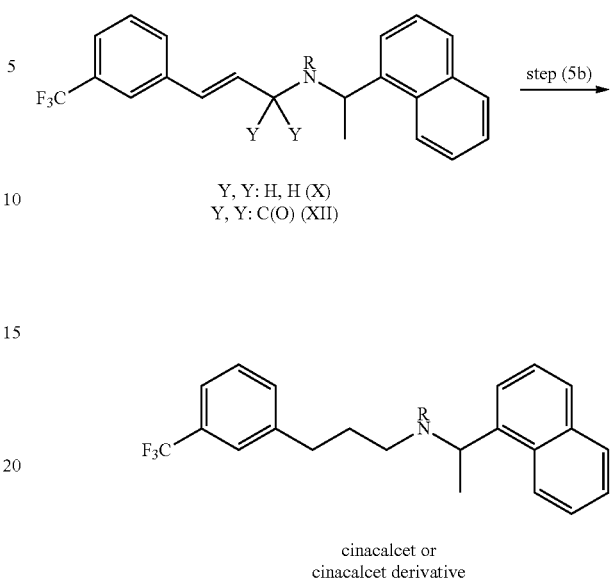

Y, Y: H, H (X)
Y, Y: C(O) (XII)

cinacalcet or
cinacalcet derivative

Compounds of formulae (IX), (XI), (X), and (XII) can independently have an R selected from hydrogen, benzyl, substituted benzyl, BOC, Cbz, and acetate. R can be any amine protecting group compatible with the various reaction conditions to which the compound is subjected. Suitable R groups (e.g., amine or amide protecting groups) include those disclosed in *Greene's Protective Groups in Organic Synthesis*, 4$^{th}$ ed (2007).

The conditions that permit the Heck coupling between the compound of formula (VIII) and the allyl amine (IX) or acrylamide (XI) include admixture in the presence of a transition metal catalyst. Typically, the transition metal catalyst comprises Pd or Ru. Specific Pd catalysts include Pd(OAc)$_2$, PdCl$_2$, Pd(dba)$_3$, and Pd(P(PAr$_3$)$_4$), wherein Ar is a substituted or unsubstituted phenyl or a linked bi-phenyl phosphine, such as BINAP or dppp. Specific Ru catalysts include, but are not limited to, [RuCl$_2$(p-cymene)]$_2$. Typically a polar organic solvent is used, such as DMF, methanol, acetonitrile, or mixtures thereof. The temperature can optionally be elevated to assist in formation of the compound of formula (X) or (XII). Additionally, a base can also be added to facilitate the Heck reaction. Bases include amine bases, such as triethylamine or diisopropylethylamine, or metal carbonates (e.g., potassium carbonate), or metal acetates (e.g., sodium acetate).

The reduction of step (5b) can be performed under the conditions as described above for step (1c) and/or step 4(b).

Alkene Reduction

An alternate route to the synthesis of cinacalcet is outlined in Scheme 6, below. It involves the reduction of an alkyne compound of formula (XIII) or formula (XVI) to form cinacalcet or a cinacalcet derivative. For compounds of formulae (XIII) or (XVI), R can be hydrogen, benzyl, substituted benzyl, Cbz, BOC, and acetate, or any amine protecting group which is compatible with the reaction conditions to which the compound is subjected. Suitable amine protecting groups include, but are not limited to, those disclosed in *Greene's Protective Groups in Organic Synthesis*, 4$^{th}$ ed (2007).

Scheme 6

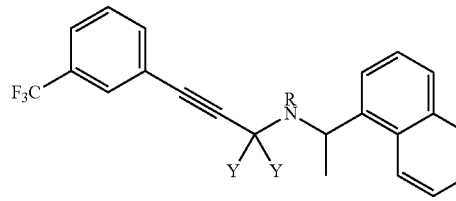

Y, Y: H, H (XVI)
Y, Y: C(O) (XIII)

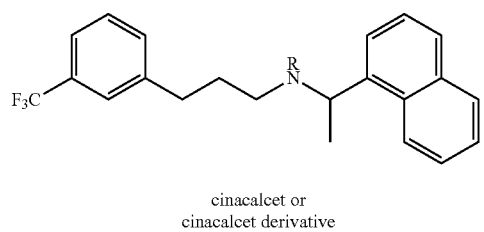

cinacalcet or
cinacalcet derivative

The reduction conditions of step (6a) can be as those described above for steps (1c), (4b), or (5b). Similar to steps (4b) and (5b), the reduction of the alkyne compound of formula (XIII) or (XVI) can be achieved in a step-wise manner, with each successive reduction intermediate isolated prior to a subsequent reduction. For example, for a compound of formula (XIII), the carbonyl moiety of the compound can be reduced to a methylene moiety (to form a compound of formula (XVI)) prior to reduction of the alkyne bond. The alkyne bond can be first reduced to an alkene (to form a compound of formula (IV)), isolated as such, then to an alkyl group to form cinacalcet. Alternatively, the alkyne compound of formula (XIII) can be reduced first, to an alkene (to form a compound of formula (VIIB)), isolated as such, then reduced to an alkyl group (to form a compound of formula (VIIA)), and then the carbonyl moiety can be reduced to form cinacalcet or a cinacalcet derivative.

In various embodiments, the compound of formula (XIII) is prepared prior to reduction to cinacalcet. Schemes 6A-6D outline several routes for the preparation of a compound of formula (XIII) or (XVI).

Scheme 6A

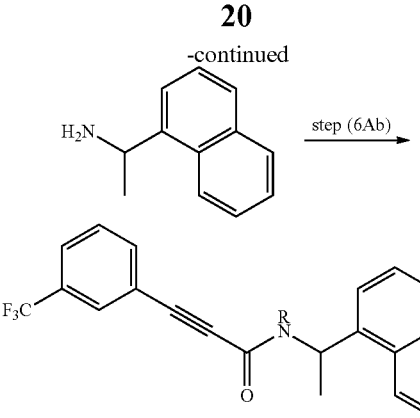

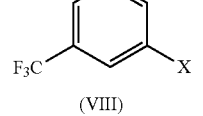

(XIII)

Scheme 6B

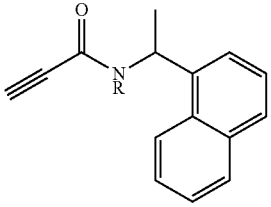

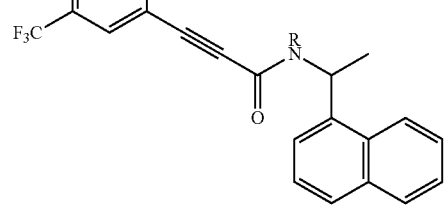

(XIII)

The coupling of step (6Aa) or (6Ba) can be performed in the presence of a transition metal catalyst. Such catalysts include a PdCl$_2$ catalysts, optionally having one or more phosphine ligands, and a co-catalyst, such as a copper salt (e.g., CuI). An inorganic or amine base may also be used to facilitate the coupling of the compound of formula (VIII) and (XV) the propiolic acid or ester. Such bases include Et$_3$N, metal carbonates (e.g., Cs$_2$CO$_3$), and metal bicarbonates (e.g., NaHCO$_3$). Other conditions can be used which include exposing to microwave energy and/or heating to above 50° C.

Step (6Ab) can be performed using similar conditions for peptide bond formation as described above, for step (4a).

Scheme 6C

21
-continued

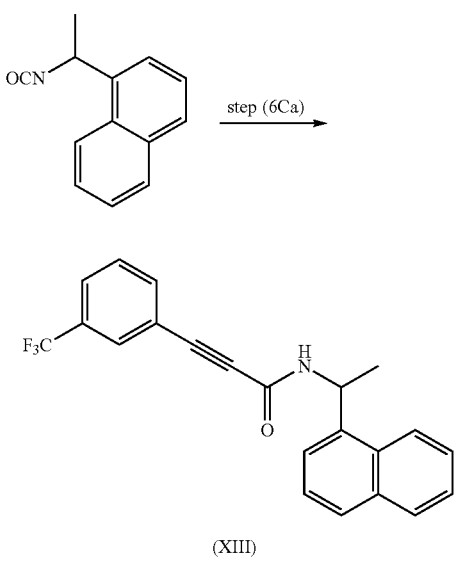

(XIII)

Alternatively, a compound of formula (XIII) can be prepared by reacting 3-trifluoromethylphenyl acetylene and 1-(1-naphthyl)ethyl isocyanate. In various embodiments, 3-trifluoromethylphenyl acetylene is admixed with a base, such as n-butyl lithium or a Grignard reagent, to form a deprotonated acetylide. The acetylide is then admixed with the isocyanate to form the compound of formula (XIII), wherein R is hydrogen, as shown in Scheme 6C. Other conditions suitable for isocyanate coupling to form an amide applicable to the methods described herein include those described in Debrabander et al., *Tetrahedron*, 60:9635 (2004).

In various embodiments, the compound of formula (XVI) is prepared as outlined in Scheme 6D. The Sonogashira coupling between a compound of formula (VIII) and a compound of formula (XVII), step (6Da), can provide a compound of formula (XVI). The conditions for the Sonogashira coupling are as described above, for step (6Aa) or (6Ba). R can be a hydrogen, a $C_{1-6}$alkyl, or a nitrogen protecting group, such as a Boc, Fmoc, or Cbz group, that is stable to the Sonogashira coupling conditions. Suitable protecting groups for nitrogen are discussed in detail in the *Greene's Protective Groups in Organic Synthesis*, 4$^{th}$ ed (2007).

Scheme 6D

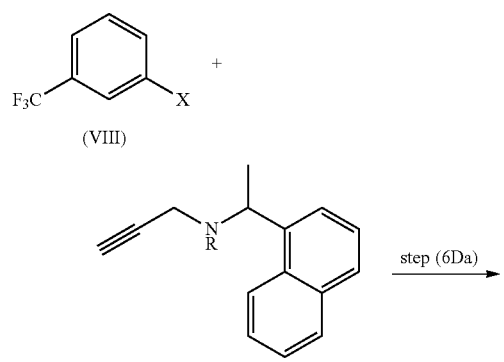

22
-continued

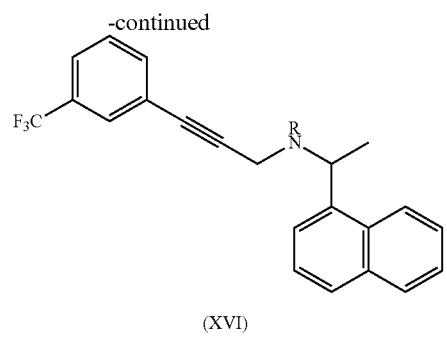

(XVI)

Cross Metathesis

Cinacalcet can be prepared via cross-metathesis of a compound of formula (I) and a compound of formula (XVIII) to form a compound formula (IV), as shown below in Scheme 7. $R^1$ is independently selected from hydrogen and $C_{1-6}$alkyl. The conditions for the cross-metathesis step (7a) is as described above for step (1a) and the conditions for forming cinacalcet from a compound of formula (IV) is described above for step (3c).

Scheme 7

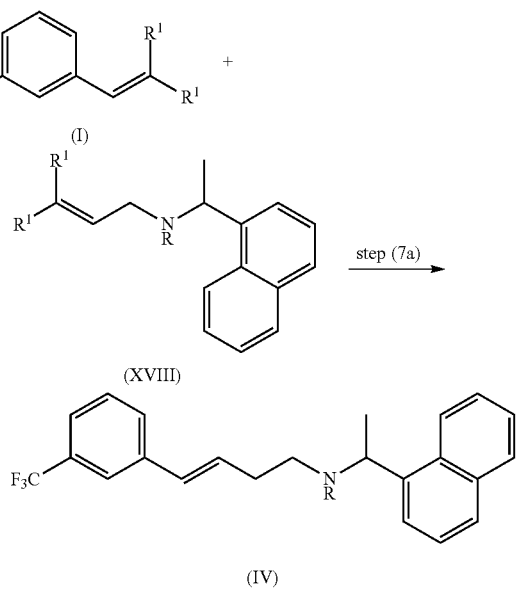

Hydroformylation

Cinacalcet can be prepared using hydroformylation, as depicted in Scheme 8, below. In various embodiments, 3-(3-trifluoromethylphenyl)propanal is prepared (step (8a)), then admixed with 1-(1-naphthyl)ethylamine to form an imine (XX) (step (8b)), which can be reduced to form cinacalcet (step (8c)). Hydroformylation conditions can include exposure to a mixture of hydrogen gas and carbon monoxide in the presence of a metal catalyst. Typically, the metal is a cobalt or rhodium catalyst. Examples of ligands in the catalyst can include phosphine ($PR_3$, $RC_6H_5$, n-$C_4H_9$), phosphine oxide (O=P($C_6H_5$)$_3$), phosphite, amine, amide, and isonitrile. Other conditions suitable for hydroformylation applicable to the methods described herein include those described in U.S. Pat. Nos. 4,148,830; 4,717,775; 4,769,498, and WO 03/078444. The reduction of the compound of formula (XX) can be accomplished using the conditions as outlined above for steps (1c), or can be accomplished by reduction with a hydride reducing agent such as sodium borohydride, sodium (triacetoxyborohydride), sodium (cyanoborohydride), disobutylaluminium hydride or lithium aluminium hydride Scheme 8

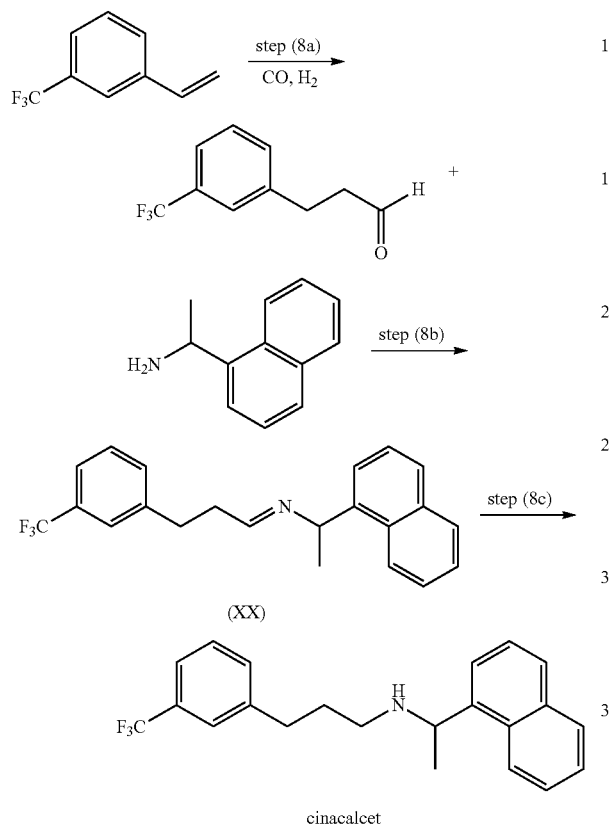

cinacalcet

In various embodiments, the 3-trifluoromethylstyrene, hydrogen, carbon monoxide and 1-(1-naphthyl)ethyl amine are all admixed together to form cinacalcet without isolating the intermediate compound of formula (XX), as shown in Scheme 8A, below. The conditions of step (8Aa) are heating the substrates in the presence of [Rh(cod)$_2$]BF$_4$, and a phosphine ligand such as Xantphos under elevated pressure of carbon monoxide and hydrogen. Other conditions suitable for the hydroaminomethyalation are described in Ahmed et al., *J. Am. Chem. Soc.* 125:10311 (2003) and Briggs, et al. *Org. Lett.*, 7:4795 (2005).

Scheme 8A

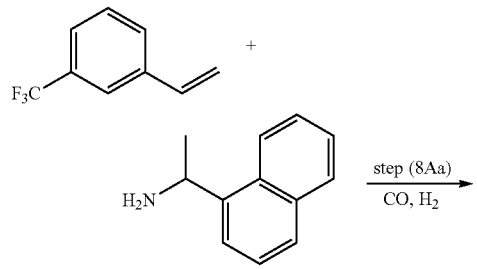

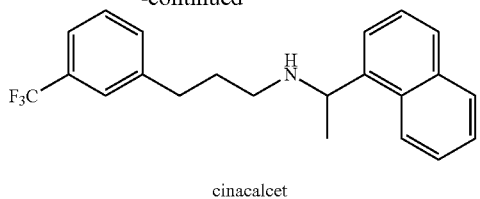

cinacalcet

Acrylamide Coupling

In various embodiments, cinacalcet can be synthesized as depicted in Scheme 9, below. Coupling of compound (VIIIA) and compound (XIA) can be accomplished by admixing compound (VIIIA) and compound (XIA) in the presence of a rhodium catalyst to form compound (VII). Compound (VII) then can be reduced to form cinacalcet or a salt thereof.

Scheme 9

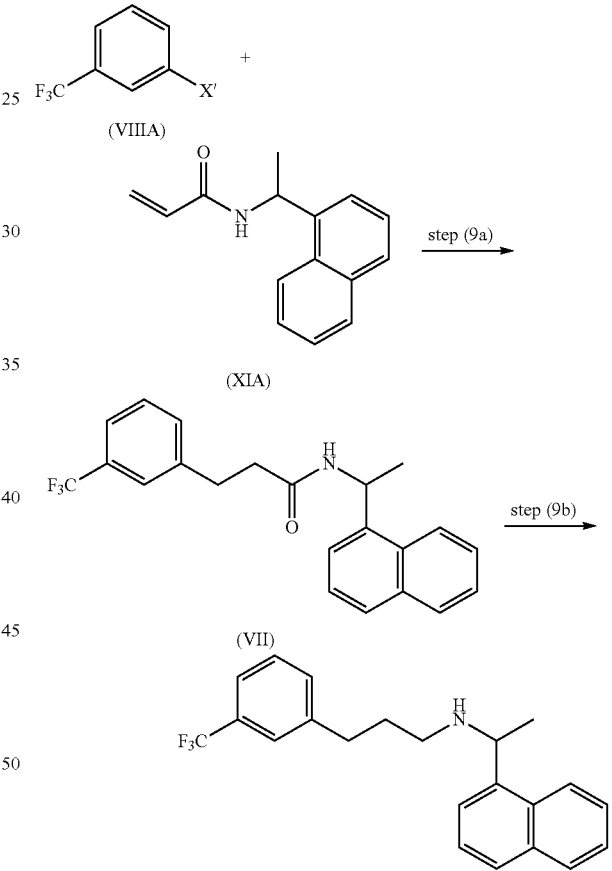

cinacalcet

For compound (VIIIA), X' can be B(OH)$_2$, Si(OR$^3$)$_3$, Sn(R$^3$)$_3$, and Ti(OR$^3$)$_3$, and R$^3$ is the same or different and is independently selected from the group consisting of hydrogen and C$_{1-6}$alkyl.

The conditions that promote coupling of compounds (VIIIA) and (XIA) can include admixture of the compounds in the presence of a rhodium or palladium catalyst. The rhodium catalyst can be a rhodium (I) catalyst, for example. Specific Rh catalysts include, but are not limited to, Rh(acac)(CO)$_2$, Rh(acac)(C$_2$H$_4$)$_2$, or Rh(acac). Specific Pd catalysts include Pd(OAc)$_2$, which can be coordinated to a nitrogen ligand, such as bipyridine, 1,10-phenanthroline, and bisoxazolines. In a specific class of embodiments, the Rh catalyst can be coordinated to a phosphorus ligand, such as PPh$_3$, PCy$_3$, BINAP, diop, chiraphos, MeO-mop, iPr-phox, or bppfa. Other conditions include those disclosed in Sakuma, et al., *J. Org. Chem.*, 66:8944-8946 (2001), Hayashi, et al., *Chem. Rev.*, 103:2829-2844 (2003), Lautens, et al., *Synthesis*, 12:2006-2014 (2004), and Lu, et al., *J. Org. Chem.*, 70:9651-9653 (2005).

The conditions that permit reduction can include performing the reduction in the presence of a reducing agent. Reducing agents include, but are not limited to, metal hydrides such as sodium borohydride (NaBH$_4$), lithium borohydride (LiBH$_4$), calcium borohydride (Ca(BH$_4$)$_2$), lithium aluminum hydride (LiAlH$_4$) or complexes of BH$_3$ with THF, Et$_3$N or Me$_2$S.

Hydroboration

In various embodiments, cinacalcet can be synthesized as depicted in Scheme 10, below. Hydroboration of 1-(3-trifluoromethylphenyl)-2-propene is accomplished by admixing the allylbenzene with borane. Next, N-chloro-1-(1-naphthyl)ethylamine is added to the mixture to form cinacalcet.

Scheme 10

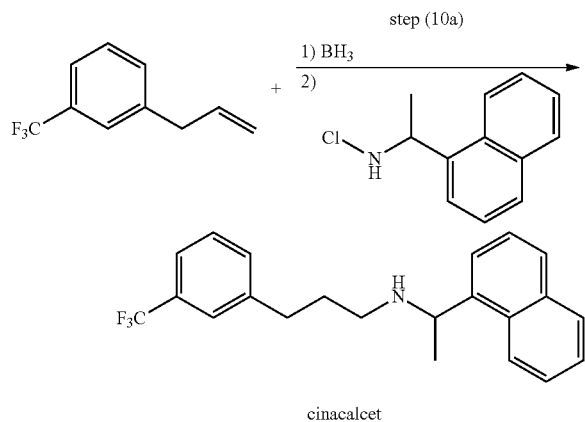

cinacalcet

Hydroboration conditions for step (10a) include hydroboration conditions such as those disclosed in Kabalka et al., *J. Org. Chem.*, 49:1656 (1984). Boranes other than BH$_3$ can be used. Other boranes contemplated include, but are not limited to, hydroboration reagents R$_2$BH, such as dicyclohexylborane, diisopropylborane, disiamylborane, 9-borabicyclo[3.3.1]nonane ("9-BBN"), and the like. Hydroborations are generically discussed in Miyaura er al. *Chem. Reviews*, 2457 2483 (1995).

Cinacalcet Salts

Cinacalcet can also be made by one or more of the methods disclosed herein and formulated as pharmaceutically acceptable salts (e.g., acid addition salts) and complexes thereof. Pharmaceutically acceptable salts are non-toxic salts at the concentration at which they are administered. The preparation of such salts can facilitate the pharmacological use by altering the physical characteristic of the cinacalcet without preventing it from exerting its physiological effect. Useful alterations in physical properties include lowering the melting point to facilitate transmucosal administration and increasing the solubility to facilitate administering higher concentrations of the drug.

Pharmaceutically acceptable salts include acid addition salts such as those containing sulfate, hydrochloride, phosphate, sulfamate, acetate, citrate, lactate, tartrate, methanesulfonate, ethanesulfonate, benzenesulfonate, p-toluenesulfonate, cyclohexylsulfamate and quinate. (See e.g., WO 92/020642.) Pharmaceutically acceptable salts can be obtained from acids such as hydrochloric acid, sulfuric acid, phosphoric acid, sulfamic acid, acetic acid, citric acid, lactic acid, tartaric acid, malonic acid, methanesulfonic acid, ethanesulfonic acid, benzenesulfonic acid, p-toluenesulfonic acid, cyclohexylsulfamic acid, and quinic acid. In preferred embodiments, the salt is the hydrochloride salt.

Pharmaceutically acceptable salts can be prepared by standard techniques. For example, the free base form of a compound is dissolved in a suitable solvent, such as an aqueous or aqueous-alcohol solution, containing the appropriate acid and then isolated by evaporating the solution. In another example, a salt is prepared by reacting the free base and acid in an organic solvent.

Cinacalcet Polymorphs

Three distinct crystalline forms of cinacalcet HCl are currently known, and are referred to herein as Forms I, II, and III, and can be referred to as "polymorphs." Form II has been prepared but was unstable at room temperature. Since the intended use of cinacalcet is as a therapeutically active pharmaceutical agent, a stable and pharmaceutically acceptable form of this compound is a preferred embodiment.

Polymorphism can be characterized as the ability of a compound to crystallize into different crystal forms, while maintaining the same chemical formula. A crystalline polymorph of a given drug substance is chemically identical to any other crystalline polymorph of that drug substance in containing the same atoms bonded to one another in the same way, but differs in its crystal forms, which can affect one or more physical properties, such as stability, solubility, melting point, bulk density, flow properties, bioavailability, etc. Thus, the term "polymorph" is used to refer to a crystalline form of a substance that is distinct from another crystalline form but that shares the same chemical formula.

While the present invention particularly contemplates an isolated composition of a purified cinacalcet hydrochloride polymorph III, it is contemplated that the skilled person may prepare compositions in which the isolated, purified polymorph III is mixed with, for example, polymorph I or II.

In addition, in compositions for use in the present invention, it should be understood that the skilled person may prepare pharmaceutical or other therapeutic compositions which comprise the polymorph III described herein in combination with another agent that is used as a calcimimetic. Such combination therapy compositions may be used to have a combined effect as a calcimimetic combination therapy to produce a desired therapeutic, ameliorative, inhibitory or preventative PTH-lowering or calcium-lowering effect.

In the therapeutic embodiments of the invention, the compositions can be administered and the effects of the compositions are routinely monitored to avoid the subject becoming hypocalcemic; therefore lowering the serum calcium levels to less than 7.8 mg/dL should be avoided. In other embodiments, the calcimimetic therapy is administered to lower the PTH levels in the subject, and the PTH levels are lowered to levels of about 250 pg/ml. However, the therapies should be monitored and adjusted to avoid lowering the PTH levels to less than 150 pg/ml. Thus, the therapies preferably are designed in order to lower and maintain the PTH levels to a range of about 200 pg/ml to about 300 pg/ml.

Thus, in a typical treatment regimen, it is contemplated that a daily dose of the polymorph III is administered to achieve PTH levels in the subject of about 150 pg/ml to about 300 pg/ml. Thus, in various embodiments, the subject is initiated on a therapeutic regimen in which a dosage form of about 5 mg, 10 mg, 15 mg, 20 mg, 25 mg, or 30 mg is administered daily. The PTH levels in the subject are monitored prior to and after administration of the composition. The dosage of the polymorph can be increased to a level at which the dosage has the desired therapeutic effect of maintaining the level of PTH of about 200 pg/ml to about 300 pg/ml. Where it is seen that the PTH levels in the subject are higher than 300 pg/ml, the dosage of the polymorph administered may be increased. If the level of the PTH is seen to be at or about 200 pg/ml, the dosage of the polymorph can be maintained or lowered. If the level of the PTH is seen to be below 200 pg/ml, the dosage of the polymorph should be lowered. The PTH concentration can be monitored and the polymorph administration regimen reinitiated when and if the patient's PTH levels again reach 300 pg/ml or greater. Likewise, the serum calcium levels can be monitored in response to the treatment with the polymorph III such that the serum calcium levels are maintained at or above the lower limit of the normal level of serum calcium, which is about 8.4 mg/dL. If the blood work shows that the treatment with the polymorph is resulting in the decrease of serum calcium levels to the range of between 7.8 mg/dL to about 8.4 mg/dL the dosage of the polymorph should be decreased and/or combined with calcium-containing phosphate binders and/or vitamin D sterols. If the calcium levels fall below 7.5 mg/dL the calcimimetic therapy should be stopped and/or the amount of vitamin D sterols and/or calcium-containing phosphate binders should be increased until the serum calcium levels are again above 8.4 mg/dL.

As used herein, the term "amorphous" refers to samples lacking a well-defined peak or having a broad "halo" feature in the X-ray powder diffraction (XRPD) pattern of the sample. The term "amorphous" may also refer to a material that contains too little crystal content to yield a discernable pattern by XRPD or other diffraction techniques. Glassy materials are contemplated to be amorphous. Amorphous materials do not have a true crystal lattice, and are consequently glassy rather than true solids, technically resembling very viscous non-crystalline liquids. Rather than true solids, glasses may better be described as quasi-solid amorphous material. Thus, an amorphous material may refer to a quasi-solid glassy material. Precipitation of a compound from solution, often effected by rapid evaporation of solvent, is known to favor amorphous forms of a compound.

As used herein, the term "broad" or "broadened" is used to describe spectral lines (peaks) including XRPD, nuclear magnetic resonance (NMR) spectroscopy and infrared (IR) spectroscopy lines is a relative term that relates to the line width of a baseline spectrum. The baseline spectrum is often that of an unmanipulated crystalline (defined below) form of a specific compound as obtained directly from a given set of physical and chemical conditions, including solvent composition and properties such as temperature and pressure, for example describing the XRPD spectrum of ground or pulverized crystalline material relative to the crystalline material prior to grinding. Line broadening is indicative of increased randomness in the orientation of the chemical moieties of the compound, thus indicative of an increased amorphous content. When comparisons are made between crystalline materials obtained via different crystallization conditions, broadening indicates either increased amorphous content of the sample having the broadened spectral lines, or possibly a mixture of crystals that have similar, although not identical spectra.

The specific crystal form of the agent will dictate the thermodynamic stability of the crystal. Depending on the form of the specific type of crystal present, various amounts of amorphous solid material containing the specific compound will be present. Such amorphous solid material may be present as a side product of the initial crystallization, and/or a product of degradation of the crystals comprising the crystalline material. Thus, "crystalline" as used herein contemplates amorphous content of varying degrees so long as the material has a discernable diffraction pattern. Often the amorphous content of a crystalline material may be increased by grinding or pulverizing the material, which is evidenced by broadening of diffraction and other spectral lines relative to the unground crystalline material. Sufficient grinding and/or pulverizing may broaden the lines relative to the unground crystalline material to the extent that the XRPD or other crystal specific spectrum may become undiscernable, making the material substantially amorphous, or barely discernable, which may be termed quasi-amorphous.

As used herein, the term "trace" refers to an amount that is detectable by the physical and chemical detection methods employed herein. For example, water, crystallization solvents, and amorphous forms of cinacalcet may all be present in trace amounts of Form III while not significantly affecting the XRPD, NMR, or IR spectral measurements of the sample or its biological activity.

In some instances, the polymorph may be a crystalline anhydrate, monohydrate, or hemihydrate. Amorphous polymorphs can be derived by rapidly evaporating solvent from solvated cinacalcet, or by grinding, pulverizing or otherwise physically pressurizing or abrading any of the various crystalline amorphous forms described herein. General methods for precipitating and crystallizing organic compounds may be applied to preparing any cinacalcet polymorphs. These general methods are known to those skilled in the art of synthetic organic chemistry and pharmaceutical formulation, and are described, for example, by J. March, "Advanced Organic Chemistry: Reactions, Mechanisms and Structure," 4th Ed. (New York: Wiley-Interscience, 1992).

In a specific class of embodiments, the Form III is prepared using "cold finger sublimation." Sublimation is the term used for transformation of a compound directly from the solid to the gaseous state or from the gaseous to the solid state without becoming a liquid. The apparatus for performing this process typically has a section where the compound to be sublimed is placed and a cooler section above this section where the purified material will collect. Typically, the compound is heated and collected on a chilled piece called a cold finger, thus, the "cold finger" is a common name for a chilled tubing used in the sublimation experiment. In the preparation of cinacalcet form III, the solid Form I is heated to gaseous state in a flask under vacuum and the crystal Form III accumulates on the surface of the cold finger that is inserted in the flask. Usually cooling water or dry ice are used to cool the cold finger. Polymorph III may be obtained in the following manner. Sublimation of Form I leads to formation of Form III. Sublimation was carried out on the Form I material on a laboratory scale using a cold finger sublimation apparatus. The apparatus was immersed in a silicone oil bath and the cold finger was water-cooled. The system was sealed under vacuum. Vacuum was not released until the final solids were harvested. The solids were observed through optical microscopy and characterized by XRPD analysis.

In another specific class of other embodiments, the Form III is prepared from melt-quenched amorphous material. In this process, Form I is melted at approximately 190-200° C. It is then quenched in cold bath (dry ice+acetone) for at least 15 minutes. The material is then ground into a fine powder, which is then heated at 90° C. for approximately 3.5 hours to produce the Form III.

Form III of cinacalcet is a metastable form. While a variety of solvent systems and crystallization methods were utilized, a short-range ordered material was observed by XRPD analysis. The XRPD patterns observed in the capillary screen were all similar to the pattern observed for the initial Form III crystal. Additional thermal treatment of selected capillaries did not appear to produce a different material as determined by optical microscopy and subsequent XRPD analysis.

Crystals of cinacalcet Form III suitable for structure determination were obtained from a cold finger sublimation of Form I solids. The crystal structure of Form III contains two cinacalcet HCl molecules in the asymmetric unit. The difference between the two molecules is that the aromatic ring containing the trifluoromethyl group is rotated approximately 180°. The Form III molecules have a layered packing motif and are connected through one-dimensional hydrogen bonding interactions.

Preparation of amorphous samples was attempted through a number of techniques: namely, melt/quench, spray drying and also cryogenic grinding of Form I solids. All three techniques yielded the amorphous material, which could then be used to prepare the Form III. The cryogrind, melt/quench, and spray dried materials were analyzed by XRPD, but also could be analyzed by variable-temperature XRPD, to determine a relationship between the crystalline and short-range ordered materials. Pure Form III was readily prepared from amorphous material that is made using melt/quench and the spray dried techniques. The cryogenic grinding technique tends to yield mixtures of the Form I and Form III.

As noted above, one method of preparing Form III is to use melt-quenched amorphous material. To prepare melt/quenched amorphous material, Form I is melted at 190-200° C. It is then quenched in an ice bath (dry ice+acetone) for at least 15 minutes. The process produces the amorphous material which can then be used to prepare Form III.

In the cryogenic grinding procedure, Form I is freeze-milled under liquid nitrogen for approximately 40 minutes. This produces amorphous material that can then be used to prepare Form III. The Form III is prepared by heating the amorphous form at 90° C. for 3.5 hours. This procedure tends to yield a mixture of Form I and Form III.

In another exemplary procedure for preparing amorphous material, spray-drying can be used. In an exemplary spray drying technique 10 mg/mL Form I solution in toluene solvent was spray dried and collected under the conditions shown in the following Table.

TABLE

| | |
|---|---|
| $N_2$ drying flow rate: | 350 SLPM-550 SLPM (standard L/min) |
| Atom Pressure ($N_2$): | 30-50 psi (lb/in$^2$) (0.2-0.34 MPa) |
| Inlet T: | 165° C. |
| Outlet T: | ~108° C. |
| Flow rate: | 0.5-1.0 mg/min |
| Nozzle T (bath): | 20° C. |
| Cyclone T (bath): | 20° C. |

Again, the amorphous material that results from the spray drying technique is then used to prepare Form III as discussed above, e.g., heating at 90° C. for 3.5 hours.

X-ray powder diffraction analyses were performed using a Shimadzu XRD-6000 X-ray powder diffractometer using Cu Kα radiation. The instrument is equipped with a long fine focus X-ray tube. The tube voltage and amperage were set to 40 kV and 40 mA, respectively. The divergence and scattering slits were set at 1° and the receiving slit was set at 0.15 mm. Diffracted radiation was detected by a NaI scintillation detector. A θ-2θ continuous scan at 3°/min (0.4 sec/0.02° step) from 2.5° to 40°2θ was used. A silicon standard was analyzed to check the instrument alignment. Data were collected and analyzed using XRD-6000 v.4.1. Samples were prepared for analysis by placing them in an aluminum holder with silicon insert.

X-ray powder diffraction analyses also were performed using an Inel XRG-3000 diffractometer equipped with a CPS (Curved Position Sensitive) detector with a 2θ range of 120°. Real time data were collected using Cu-Kα radiation starting at approximately 4°2θ at a resolution of 0.03°2θ. The tube voltage and amperage were set to 40 kV and 30 mA, respectively. The monochromator slit was set at 5 mm (or 2 mm) by 160 µm. The pattern is displayed from 2.5°-40°2θ. Samples were prepared for analysis by packing them into glass capillaries 1.0 mm in diameter. Each capillary was mounted onto a goniometer head that is motorized to permit spinning of the capillary during data acquisition. The samples were analyzed for 5 min. Instrument calibration was performed using a silicon reference standard.

X-ray powder diffraction analyses also were performed on prepared capillaries using a Bruker D-8 Discover diffractometer and Bruker's General Area Diffraction Detection System (GADDS, v. 4.1.14). An incident beam of Cu Kα radiation was produced using a fine-focus tube (40 kV, 40 mA), a Gael mirror, and a 0.5 mm double-pinhole collimator. Capillaries were positioned on a capillary holder secured to a translation stage. A video camera and laser were used to position the area of interest to intersect the incident beam. Samples were analyzed in transmission mode using a constant detector angle (2θ) of 20°. The incident beam was scanned 10° relative to the capillary surface normal and rastered ±1.0 mm along the length of the capillary during the analysis. Scanning and rastering the incident beam optimizes orientation statistics and maximizes the diffraction signal. Diffraction patterns were collected in 100 seconds using a Hi-Star area detector located 14.94 cm from the sample and processed using GADDS. The intensity in the GADDS image of the diffraction pattern was integrated from approximately 2° to 37° 2θ and from −163° to −17° chi using a step size of 0.04° 2θ. The integrated patterns display diffraction intensity as a function of 2θ.

Variable-temperature XRPD (VT-XRPD) was performed on a Shimadzu XRD-6000 X-ray powder diffractometer equipped with an Anton Paar HTK 1200 high temperature stage. The sample was packed in a ceramic holder and analyzed from 2.5° to 40°2θ at 3°/min (0.4 sec/0.02° step). Ramp rates and hold times for each experiment may be varied and such variations are known to those of skill in the art of operating X-ray powder diffractometer equipment. A silicon standard was analyzed to check the instrument alignment. Temperature calibration was performed using vanillin and sulfapyridine standards. Data were collected and analyzed using XRD-6000 v.4.1. VT-XRPD was performed on as-received short-range ordered material as well as materials prepared through quenching of a melt and cryogenic grinding.

Differential scanning calorimetry (DSC) also can be performed for the crystalline materials using a TA Instruments differential scanning calorimeter 2920, or other similar instrument. The sample was placed into an aluminum DSC pan, and the weight accurately recorded. The pan was covered with a lid and then crimped. In such an analysis, the sample cell is equilibrated at 25° C. and heated under a nitrogen purge at a rate of 10° C./min. The crystalline material is typically heated to 350° C., and transition maxima temperatures are noted.

Thermogravimetric (TG) analysis can be performed for crystalline material using a TA Instruments 2950 thermogravimetric analyzer or other similar instrument. The sample is placed in an aluminum sample pan and inserted into the TG furnace. The furnace is first equilibrated at 25° C., then heated under nitrogen at a rate of 10° C./min, up to a final temperature of 350° C. Nickel and Alumel™ can be used as the calibration standards.

FT-Raman spectrum also can be acquired for the polymorph III on an FT-Raman 960 spectrometer (Thermo Nicolet) or other similar instrument. This spectrometer uses an excitation wavelength of 1064 nm. Approximately 0.7 W of Nd:YVO4 laser power is used to irradiate the sample. The Raman spectrum is measured with an indium gallium arsenide (InGaAs) detector. The sample is prepared for analysis by placing the material in a glass tube and positioning the tube in a gold-coated tube holder in the accessory. Sample scans (e.g., typically in the order of approximately 250 sample scans) are collected from 3600-98 $cm^{-1}$ at a spectral resolution of 4 $cm^{-1}$, using Happ-Genzel apodization. Wavelength calibration was performed using sulfur and cyclohexane.

For NMR analysis, a solution $^1H$ nuclear magnetic resonance (NMR) spectrum can be acquired at ambient temperature using e.g., a Varian $^{UNITY}$INOVA-400 or other similar spectrometer at a $^1H$ Larmor frequency of 399.804 MHz. The sample is dissolved in DMSO-$d_6$. The spectrum is acquired with a $^1H$ pulse width of 7.8 µs, a 2.50 second acquisition time, a 5 second delay between scans, a spectral width of 6400 Hz with 32000 data points, and 40 co-added scans. The free induction decay (FID) is processed using the Varian VNMR 6.1C software with 65536 points and an exponential line broadening factor of 0.2 Hz to improve the signal-to-noise ratio. The residual peak from incompletely deuterated DMSO is typically seen at approximately 2.50 ppm. The spectrum can be referenced with an internal reference, e.g., to internal tetramethylsilane (TMS) at 0.0 ppm.

The crystalline material also may be characterized using optical microscopy e.g., performed with a Leica DM LP polarizing microscope (or other similar instrument), with a 5.0× objective, crossed-polarizers and a first order red compensator and Leica stereoscopes, with 0.8× to 10× objectives, with and without crossed-polarizers and a first order red compensator. Samples can be viewed in vials or glass microbeakers, or on coverglasses or glass slides (often with a drop of the cryoprotectant PARATONE-N).

Pharmaceutical Compositions and Therapy Using Cinacalcet

The disclosure further provides pharmaceutical compositions and formulations using such polymorphs. The pharmaceutical compositions and formulations are adapted for various forms of administration including oral, injection and/or inhalation. The disclosure also provides methods for making cinacalcet hydrochloride polymorph, methods of manufacturing pharmaceutical formulations of cinacalcet hydrochloride polymorph and methods of treating various diseases such as, for example, HPT, parathyroid carcinoma, and other hypercalcemia-related disorders.

"Effective" or "therapeutically effective" is meant to describe a polymorph of a compound or a composition of the present invention effective as a calcimimetic and thus producing the desired therapeutic, ameliorative, inhibitory or preventative effect of Sensipar®. While the level or degree of calcimimetic, therapeutic, ameliorative, inhibitory or preventative effect in various embodiments is the same or better than that seen when Sensipar® is used, the level or degree of such an effect may be less than that observed with Sensipar® as long as it is more than, or better than the effect seen in the absence of any calcimimetic. The "effect" may be a biochemical physiologic effect such as a lowering of serum calcium levels in a hypercalcemic patient, lowering of PTH levels, or lowering of serum phosphorus levels. Alternatively, the "effect" may be one that is observed as a result of achieving a therapeutic lowering of serum calcium levels, PTH levels and the like, such as for example, an amelioration of the symptoms of CKD, a decrease in symptoms associated with increased calcium levels (e.g., lowering of anxiety, depression, nausea, vomiting, bone fractures, kidney stones, vascular or soft-tissue calcification, and in some cases decreased likelihood of coma).

In one aspect, the polymorph Form III of the invention is able to modulate calcium receptor activity and is used in the treatment of diseases or disorders which can be affected by modulating one or more activities of a calcium receptor. As noted above, $Ca^{2+}$ levels are tightly controlled and $Ca^{2+}$ levels in turn control various processes such as blood clotting, nerve and muscle excitability, and proper bone formation. For example, extracellular $Ca^{2+}$ inhibits the secretion of parathyroid hormone from parathyroid cells, inhibits bone resorption by osteoclasts, and stimulates secretion of calcitonin from C-cells. In one aspect, the disease or disorder to be treated by cinacalcet can be characterized by abnormal bone and mineral homeostasis, such as calcium homeostasis. Abnormal calcium homeostasis is characterized by one or more of the following activities: (1) an abnormal increase or decrease in serum calcium; (2) an abnormal increase or decrease in urinary excretion of calcium; (3) an abnormal increase or decrease in bone calcium levels, for example, as assessed by bone mineral density measurements; (4) an abnormal absorption of dietary calcium; (5) an abnormal increase or decrease in the production and/or release of messengers which affect serum calcium levels such as parathyroid hormone and calcitonin; and (6) an abnormal change in the response elicited by messengers which affect serum calcium levels. The abnormal increase or decrease in these different aspects of calcium homeostasis is relative to that occurring in the general population and is generally associated with a disease or disorder.

Specific diseases and disorders which might be treated or prevented, based upon the affected cells, also include those of the central nervous system such as seizures, stroke, head trauma, spinal cord injury, hypoxia-induced nerve cell damage such as in cardiac arrest or neonatal distress, epilepsy, neurodegenerative diseases such as Alzheimer's disease, Huntington's disease and Parkinson's disease, dementia, muscle tension, depression, anxiety, panic disorder, obsessive-compulsive disorder, post-traumatic stress disorder, schizophrenia, neuroleptic malignant syndrome, and Tourette's syndrome; diseases involving excess water reabsorption by the kidney such as syndrome of inappropriate ADH secretion (SIADH), cirrhosis, congestive heart failure, and nephrosis; hypertension; preventing and/or decreasing renal toxicity from cationic antibiotics (e.g., aminoglycoside antibiotics); and autoimmune diseases and organ transplant rejection. In addition, bone and mineral-related disorders (as described in Coe and Favus, *Disorders of Bone and Mineral Metabolism*, Raven Press, 1990), kidney diseases, endocrine diseases, cancer, cardiovascular diseases, neurological diseases, and diseases associated with gestation also can be treated.

In certain embodiments, the compositions will be useful in treating or ameliorating psoriasis by reducing the proliferation of the abnormal skin cells. In other embodiments, the compositions may be used to reduce water retention in states of vasopressin excess, such as the syndrome of inappropriate vasopressin (ADH) secretion. Polymorph III may be useful for treating hypertension by: (a) reducing renin secretion and/or (b) by stimulating production of vasodilators such as PTHrP (PTH-related peptide) by vascular smooth muscle. It also is contemplated that the polymorph Form III may be used to increase platelet aggregability, which may be useful when platelet counts are low. Calcium also is known to promote differentiation of colon and mammary cells, as such the polymorph Form III may be expected to reduce the risk of colon or breast cancer. As a calcimimetic, cinacalcet Form III is expected to have a useful hypocalcemic action in the therapy of hypercalcemic disorders. The inhibitory effect of calcimimetics on osteoclasts and their stimulation of the secretion of the hypocalcemic peptide calcitonin make them useful in the therapy of hypercalcemia and its symptoms. The cinacalcet Form III also improves hypocalcemic symptoms by activating calcium receptors. In addition, calcium suppresses the formation of 1,25-dihydroxyvitamin D in the proximal renal tubule, and this vitamin D metabolite is frequently overproduced in renal stone patients and contributes to their hypercalciuria. Suppression of 1,25-dihydroxyvitamin D formation by a calcimimetic such as cinacalcet Form III is expected to be useful in treating renal calcium stone disease.

The therapeutic cinacalcet Form III preparations will likely be used in the treatment of human subjects but it should be understood that veterinary treatments also are contemplated and the compositions may be used to treat other primates, farm animals such as swine, cattle, and poultry; and sports animals and pets such as horses, dogs and cats.

For additional methods and compositions for using cinacalcet-related compositions and diseases to be treated by such compositions, those of skill are referred to U.S. Pat. Nos. 6,011,068; 6,031,003; 6,211,244; 6,313,146.

All patents, publications and references cited herein are hereby fully incorporated by reference. In case of conflict between the present disclosure and incorporated patents, publications and references, the present disclosure should control.

EXAMPLES

The present invention is further explained by the following examples which should not be construed by way of limiting the scope of the present invention.

Example 1

Allelic Amination

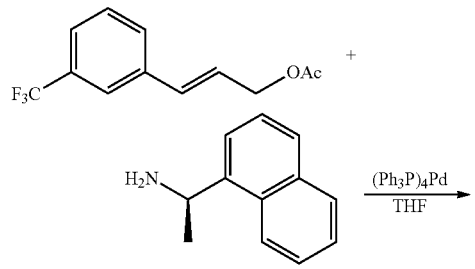

-continued

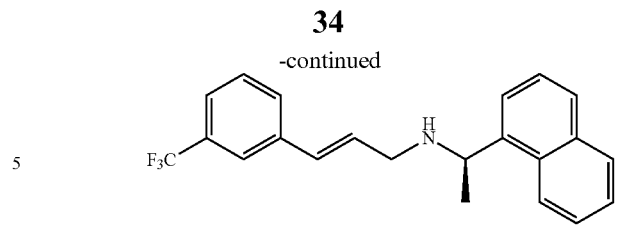

(R)-(1-Naphthyl)ethylamine (257 mg, 1.5 mmol) and 3-trifluoromethyl cinnamyl acetate (244 mg, 1 mmol) were charged to a 15 mL flask. Tetrahydrofuran (THF, 2 mL) and tetrakis(triphenylphosphine)palladium (58 mg, 5 mol %) were added, and the flask was purged with nitrogen. The reaction mixture was stirred at room temperature for 16 h. The solvents were evaporated under vacuum and the residue was dissolved in dichloromethane (10 mL). The organic phase was washed with saturated sodium bicarbonate (5 mL) and the aqueous phase was back extracted with dichloromethane (5 mL). The organic layers were dried over magnesium sulfate and evaporated to dryness. Chromatography on silica gel using dichloromethane:methanol (50:1) as eluent afforded the desired (R)-(1-naphthalen-1-yl-ethyl)-[(E)-3-(3-trifluoromethyl-phenyl)-allyl}-amine (294 mg, 98.1% HPLC purity at 254 nm, 83% uncorrected yield). The product was contaminated by some triphenylphosphine. The dialkylated product was formed as a byproduct as well.

This reaction was also performed with the branched allylic acetate. Under non-optimized conditions, the HPLC showed 40% of the N-monoalkylated product and 54.7% of the N,N-dialkylated product.

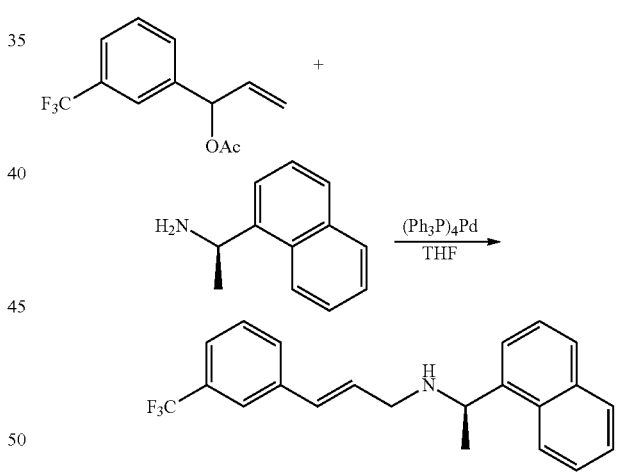

The allylic amine was then reduced in the presence of palladium on carbon and hydrogen gas in methanol to cinacalcet. The allylic amine (Didehydro-Sensipar®) (252 mg, 0.709 mmol), palladium (10 wt % on charcoal, 25 mg), and methanol (5 mL) were charged in a 15 mL flask. The reaction mixture was stirred under an atmosphere of hydrogen for 14 h. The reaction mixture was filtered through a plug of Celite® and then concentrated. Chromatography on silica gel using dichloromethane:methanol (20:1) as eluent afforded cinacalcet (229 mg, 89.3% purity by HPLC at 254 nm, 90% uncorrected yield). The product was contaminated with some triphenylphosphine.

Alternatively, cinacalcet was synthesized by a cross-coupling reaction between (R)-(+)-1-(1-napthyl)ethylamine and 1-(3-trifluoromethyl-phenyl)-prop-2-en-1-ol. The 1-(3-trifluoromethyl-phenyl)-prop-2-en-1-ol was synthesized as follows

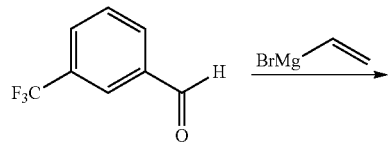

To a 1.0 M THF solution of vinylmagnesium bromide (2.2 equiv.; 37.9 mmol; 37.9 mL) cooled to 0-5° C. over an ice/water bath, was added 3-(trifluoromethyl)benzaldehyde (1.0 equiv.; 17.23 mmol; 2.29 mL) over 2 minutes. The cold bath was removed after 15 minutes and the reaction was stirred at room temperature for 2 hours. The reaction was quenched with an aqueous ammonium chloride solution. The solvent was removed in vacuo. The aqueous layer was extracted three times with 20 mL dichloromethane. The organic layer was dried over sodium sulfate, filtered and the solvent removed in vacuo. Isolated 3.17 g; as a yellow liquid, yield 91%. The product identity was confirmed by $^1$H NMR (400 MHz, CDCl$_3$) δ ppm 2.25 (br. S., 1H) 5.17-5.28 (m, 2H) 5.30-5.43 (m, 1H) 5.93-6.09 (m, 1H) 7.40-7.59 (m, 3H) 7.64 (s, 1H).

The 1-(3-trifluoromethyl-phenyl)-prop-2-en-1-ol was then allowed to react with (R)-(+)-1-(1-napthyl)ethylamine to synthesize cinacalcet. In a representative method, a dioxane solution (5 mL) of the 1-(3-trifluoromethyl-phenyl)-prop-2-en-1-ol (1.0 equiv.; 1.0 mmol; 202.17 mg) and (R)-(+)-1-(1-napthyl)ethylamine (1.5 equiv.; 1.5 mmol; 0.241 mL) was charged the catalyst Pt(cod)Cl2 (1.0 mol %; 3.7 mg) and the ligand DPEphos (2 mol5; 10.8 mg). The reaction mixture was refluxed under an atmosphere of nitrogen for 15 hours, after which time it was diluted with water followed by extraction with ethyl acetate. The combined organic layers were dried over magnesium sulfate and filtered. The solvent was removed in vacuo to give a yellow oil which was purified by silica gel chromatography with dichloromethane/methanol (49:1). Yield: Isolated 159 mg; 44% as a yellow oil. Product identity was confirmed by LC/MS (M+1): 356.4

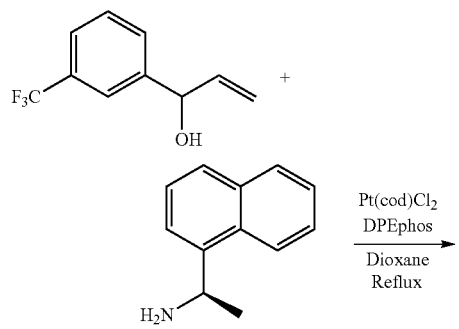

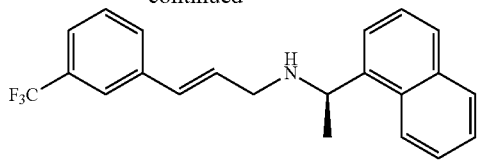

Example 2

Peptide Coupling

In an alternative embodiment the present invention provides a methodology for synthesizing cinacalcet by a reaction between the appropriate amine and a pre-activated carboxylic acid.

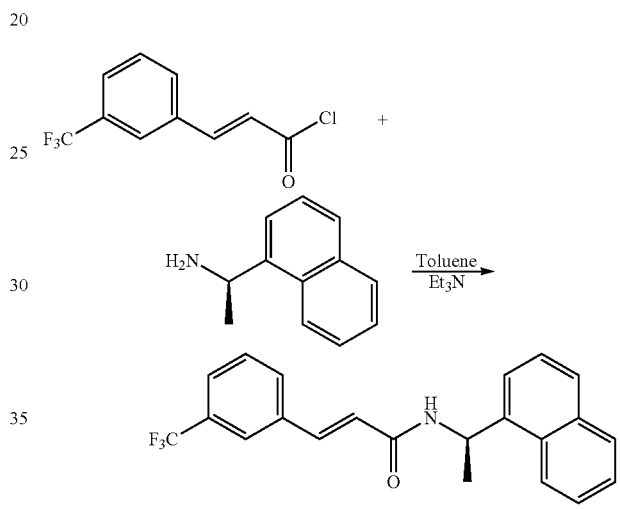

The reaction was initiated by the addition of trans-3-trifluoromethyl cinnamoyl chloride (1.0 equiv.; 21.3 mmol; 5 g) to a stirred solution of (R)-(+)-1-(1-napthyl)ethylamine (1.1 equiv.; 23.4 mmol; 4 g) and triethylamine (1.1 equiv.; 23.4 mmol; 3.26 mL) in toluene (100 mL) in an inert atmosphere of nitrogen. After stirring for 2 hours at room temperature, water (100 mL) was added to precipitate the crude product as a white solid. The solid was filtered and dried in a vacuum oven over night at 55° C. Yield: 82%; 6.49 g. The identity of (E)-N—((R)-1-Naphthalen-1-yl-ethyl)-3-(3-trifluoromethyl-phenyl)-acrylamide was confirmed by $^1$H NMR (400 MHz, CDCl$_3$) and high resolution mass spectrometry. δ ppm 1.76 (d, 3H) 5.85 (d, 1H) 6.08 (quin, 1H) 6.39 (d, 1H) 7.43-7.73 (m, 9H) 7.80-7.91 (m, 2H) 8.14 (d, 1H) and HRMS (M+1): 370.1.

In a variation of the foregoing method, the carboxylic acid can be activated in situ during the coupling reaction. For example, a 3-(trifluoromethyl)-cinnamic acid (1.0 equiv.; 2.3 mmol; 0.5 g) was activated using 1,1'-carbonyldiimidazole (1.3 equiv.; 3.0 mmol; 0.49 g) in ethyl acetate (EtOAc 10 mL). After stirring at room temperature for 3 hours, was added a solution of (R)-(+)-1-(1-napthyl)ethylamine (1.2 equiv.; 2.78 mmol; 0.45 mL). The reaction mixture was stirred at room temperature for an additional hour, with the progress of the coupling reaction monitored by LC/MS. The crude solution yield was 14% and the identity of the product was confirmed by RRT and LC/MS (M+1): 370.0.

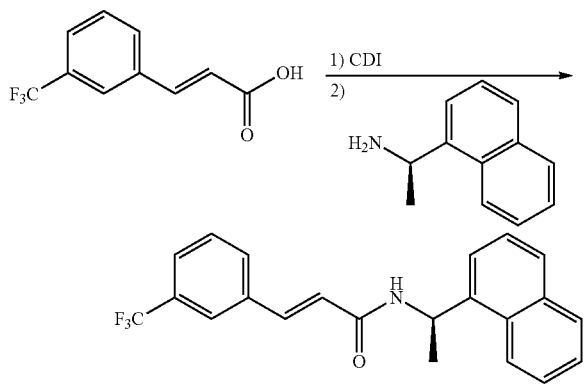

Reduction of the carbon-carbon double bond and amide group was carried out using borane as the reducing agent.

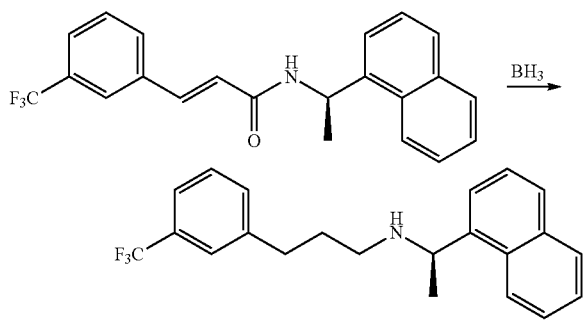

To a suspension of (E)-N—((R)-1-naphthalen-1-yl-ethyl)-3-(3-trifluoromethyl-phenyl)-acrylamide (1.0 equiv.; 0.27 mmol; 100 mg) in toluene (1 mL) was added borane-methyl sulfide complex as a 2.0M solution in toluene (1.5 equiv.; 0.44 mmol; 0.22 mL). The reaction was heated under a nitrogen atmosphere to 50° C. for 3 hours before cooling and adding 2.5N HCl (1 mL). Subsequent heating of the reaction mixture at 50° C. for 1 hour after the addition of acid, followed by analysis of the cooled reaction mixture high performance liquid chromatography-mass spectrometric detection afforded the desired saturated product. Solution yield: 93%. Confirmed identity by RRT and LC/MS (M+1): 358.4.

Alternatively, a hydride donor such as diisobutylaluminum hydride (DIBAL) can be used as the reducing agent.

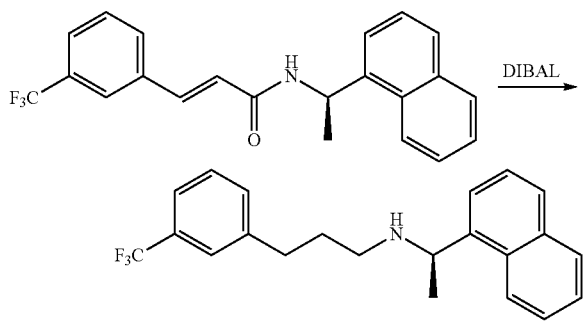

Accordingly, diisobutylaluminum hydride as a 1.0 M solution in DCM (4.25 equiv.; 5.75 mmol; 5.75 mL) was added via a syringe to a stirred suspension of (E)-N—((R)-1-naphthalen-1-yl-ethyl)-3-(3-trifluoromethyl-phenyl)-acrylamide (1.0 equiv.; 1.36 mmol; 0.5 g) in toluene (10 mL) under an inert nitrogen atmosphere. The reaction was heated to 50° C. for 90 minutes, while periodically monitoring the progress of the reaction by HPLC. Solution yield: 60%. Confirmed identity by RRT and LC/MS (M+1): 358.4

In yet another variation, the reduction of the double bond and amide carbonyl of (E)-N—((R)-1-naphthalen-1-yl-ethyl)-3-(3-trifluoromethyl-phenyl)-acrylamide is carried out in a stepwise manner. Either the carbonyl group or the alkene double bond can be reduced first. For example, the reduction of the alkene double bond is achieved by hydrogenation in the presence of a metal catalyst.

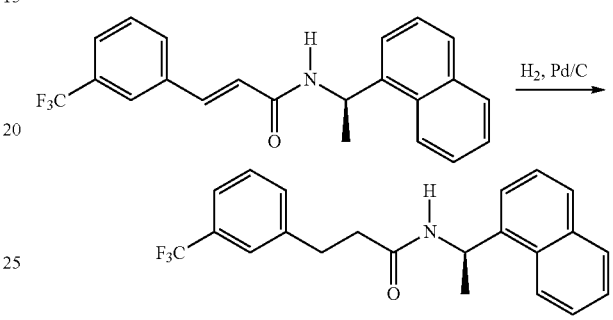

A suspension of (E)-N—((R)-1-naphthalen-1-yl-ethyl)-3-(3-trifluoromethyl-phenyl)-acrylamide (1.0 equiv.; 0.67 mmol; 250 mg) and Pd/C 10 wt % (25 mg) was stirred in a mixture of methanol and toluene (7 mL/1 mL). The reaction flask was evacuated and back filled using a hydrogen filled balloon (three times). The reaction mixture is stirred at room temperature and the progress of the reaction was monitored using high performance liquid chromatography. After 90 minutes, the reaction mixture was filtered over a bed of celite and the solvent from the filtrate was removed in vacuo. The resulting solid was dried overnight at 45° C. using a vacuum oven. Isolated yield: 91.2% (229 mg). The identity of the amide was confirmed by $^1$H NMR and mass spectrometry. (400 MHz, CDCl$_3$) δ ppm 1.60 (d, 3H) 2.39-2.53 (m, 2H) 2.96-3.13 (m, 2H) 5.55 (br. S., 1H) 5.87-5.96 (m, 1H) 7.29-7.38 (m, 2H) 7.39-7.46 (m, 4H) 7.46-7.55 (m, 2H) 7.76-7.82 (m, 1H) 7.83-7.89 (m, 1H) 8.00-8.07 (m, 1H) and HRMS (M+1): 372.1

The isolated amide is then reduced to the corresponding saturated analog (methylene moiety) using a hydride donor such as lithium aluminum hydride, sodium borohydride, or calcium hydride, as the reducing agent.

Example 3

Metal Catalyzed Cross-Coupling Reaction

Cinacalcet can be synthesized via a metal catalyzed coupling reaction between an appropriately substituted aryl halide and N—((R)-1-Naphthalen-1-yl-ethyl)-acrylamide. The acrylamide was synthesized by adding acryloyl chloride (1.2 equiv.; 17.5 mmol; 1.58 g) via syringe to an ice cold solution of (R)-(+)-1-(1-napthyl)ethylamine (2.50 g, 14.6 mmol, 1.0 eq.), and triethylamine (1.2 equiv.; 17.5 mmol; 1.77 g) in toluene (50 ml). After the addition of acryloyl chloride is complete, the reaction mixture was allowed to warm to room temperature. The reaction was quenched after stirring for an hour at room temperature by adding water (50 mL) to the reaction mixture. The crude product which precipitates out was filtered and dried in vacuo. Crude yield 79%; 3.1 g. The identity of the product was confirmed by ¹H NMR and LC/MS. (400 MHz, CDCl₃) δ ppm 1.72 (d, 3H) 5.63 (dd, 1H) 5.68-5.78 (m, 1H) 5.96-6.08 (m, 2H) 6.31 (dd, 1H) 7.42-7.59 (m, 4H) 7.77-7.89 (m, 2H) 8.11 (d, 1H) and LC/MS (M+1): 226.1.

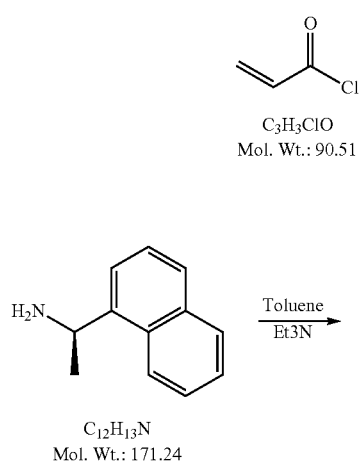

Cinacalcet was synthesized by reacting the acrylamide with 1-bromo-3-(trifluoromethyl)benzene using metal catalyzed cross-coupling conditions. In one embodiment, N—((R)-1-naphthalen-1-yl-ethyl)-acrylamide (1.0 equiv.; 0.44 mmol; 100 mg), palladium (II) acetate (5 mol %; 4.9 mg), tri-o-tolylphosphine (0.1 equiv.; 0.44 mmol; 13.4 mg) were suspended in acetonitrile (25 mL). To this suspension was added 1-bromo-3-(trifluoromethyl)benzene (1.0 equiv.; 0.44 mmol; 99 mg) and triethylamine (30 equiv.; 13.2 mmol; 1.8 mL) via syringe. The reaction was heated at reflux for 16 hours to afford (E)-N—((R)-1-Naphthalen-1-yl-ethyl)-3-(3-trifluoromethyl-phenyl)-acrylamide as the product. Solution yield: 79%. Confirmed identity by RRT and LC/MS (M+1): 370.4.

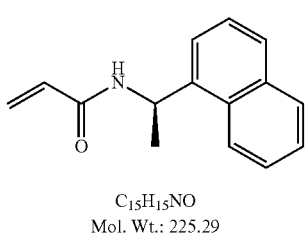

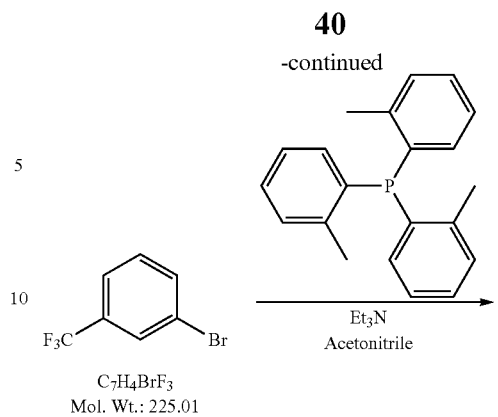

An alternative cross-coupling strategy for synthesizing cinacalcet involves the reaction of 3-(trifluoromethyl)phenyl boronic acid (3.0 equiv.; 3 mmol; 0.57 g) with N—((R)-1-naphthalen-1-yl-ethyl)-acrylamide (1.0 equiv.; 1.0 mmol; 225 mg), in the presence of palladium (II) acetate (5 mol %; 11.2 mg) and 2,2-dipyridyl (10 mol %; 15.6 mg) in glacial acetic acid (2 mL) as the catalyst. The reaction is carried out by heating the mixture under a nitrogen atmosphere at 40° C. for 3 days. At the end of the reaction the crude mixture was diluted with methanol in a volumetric flask for quantitative analysis. Solution yield: 9.1%. Confirmed identity by RRT, LCMS (M+1): 370.4

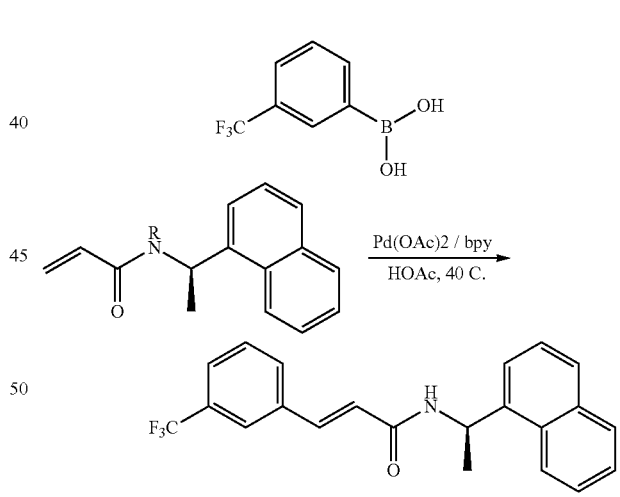

Example 4

Alkyne Reduction

The invention also provides, in another embodiment, an alternative route for synthesizing cinacalcet via the reduction of an alkyne precursor. The precursor is obtained by reacting an aryl acetylene with an appropriately substituted isocyanate. For example, a solution of 3-ethynyl-α,α,α-trifluorotoluene (0.73 mL; 5.06 mmol; 2.0 equiv.) in anhydrous THF (20 mL) was cooled to −78° C. (acetone/dry ice bath). A hexane solution of n-BuLi (1.6M, 2.69 mL; 4.30 mmol; 1.7 equiv.). is then added and the reaction mixture stirred at −78° C. for 30 minutes. A solution of (R)-1-(1-isocyanatoethyl)naphthalene (1.0 equiv.; 2.53 mmol; 0.447 mL) in THF is then added to the reaction mixture which is stirred for an additional 30 minutes at −78° C. The reaction is stopped by the addition of an aqueous solution of ammonium chloride to the organic mixture. The organic layer is repeatedly extracted with water, dried over magnesium sulfate and the solvent removed in vacuo to afford 3-(3-Trifluoromethyl-phenyl)-propynoic acid ((R)-1-naphthalen-1-yl-ethyl)-amide as product. Isolated 830 mg, 89.2% yield. The identity of the product is confirmed by $^1$H NMR and high resolution mass spectrometry. (300 MHz, CDCl$_3$) δ ppm 1.77 (d, 3H) 5.97-6.08 (m, 1H) 6.15 (br. S., 1H) 7.42-7.70 (m, 7H) 7.75 (s, 1H) 7.81-7.94 (m, 2H) 8.12 (d, 1H) and HRMS (M+1): 368.1

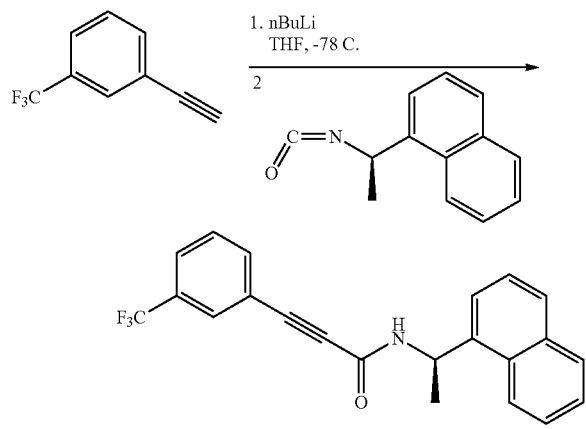

Cinacalcet is obtained by reducing the alkyne-amide precursor. In one embodiment, the alkyne was reduced by metal catalyzed hydrogenation. Specifically, to a methanolic solution (7 mL) of 3-(3-trifluoromethyl-phenyl)-propynoic acid ((R)-1-naphthalen-1-yl-ethyl)-amide (1.0 equiv.; 0.68 mmol; 250 mg) in a two necked round bottom flask was added Pd/C 10 wt % (28 mg). The flask was evacuated and back filled using a hydrogen filled balloon (three times) before stirring the reaction mixture at room temperature under a positive pressure of hydrogen. Progress of the reaction was monitored by HPLC and LC/MS, with complete reduction of the alkyne group after 1 hour. The reaction was stopped by filtering the reaction mixture over a bed of celite, and the solvent was removed to give a solid that was further dried at 45° C. overnight in vacuo. Product identity was confirmed by $^1$H NMR and LC/MS. A quantitative yield of the product was obtained (224 mg). (400 MHz, CDCl$_3$) δ ppm 1.60 (d, 3H) 2.39-2.53 (m, 2H) 2.96-3.13 (m, 2H) 5.55 (br. S., 1H) 5.87-5.96 (m, 1H) 7.29-7.38 (m, 2H) 7.39-7.46 (m, 4H) 7.46-7.55 (m, 2H) 7.76-7.82 (m, 1H) 7.83-7.89 (m, 1H) 8.00-8.07 (m, 1H) and LC/MS (M+1): 372.0.

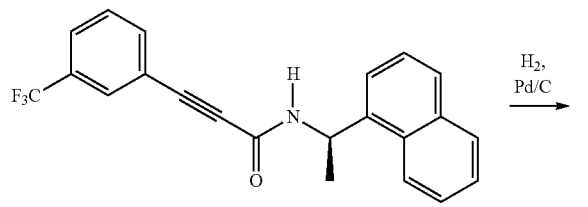

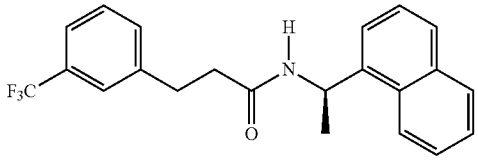

In an alternative embodiment, diborane was used as the reducing agent. Accordingly, to a stirred suspension of 3-(3-trifluoromethyl-phenyl)-propynoic acid ((R)-1-naphthalen-1-yl-ethyl)-amide (1.0 equiv.; 0.27 mmol; 100.8 mg) in toluene (2 mL) under nitrogen, was added using a borane-methyl sulfide complex as a 2.0M solution in toluene (2.5 equiv.; 0.68 mmol; 0.34 mL). The reaction was heated to 50° C. for 7 hours, and then quenched using 1N solution of HCl (1 mL) and MeOH (1 mL). The quenched reaction mixture was reheated to 90° C. for 4 hours, after which the solvent was removed in vacuo. The resulting residue was diluted with MeOH and analyzed using LC/MS and RRT to confirm the identity of the final product. Solution yield: 22%, LC/MS (M+1): 358.4

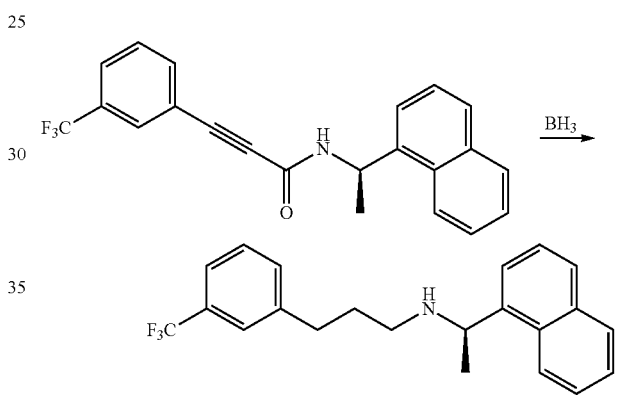

Example 5

Hydroformylation

In yet another embodiment, cinacalcet was synthesized via a hydroformylation reaction.

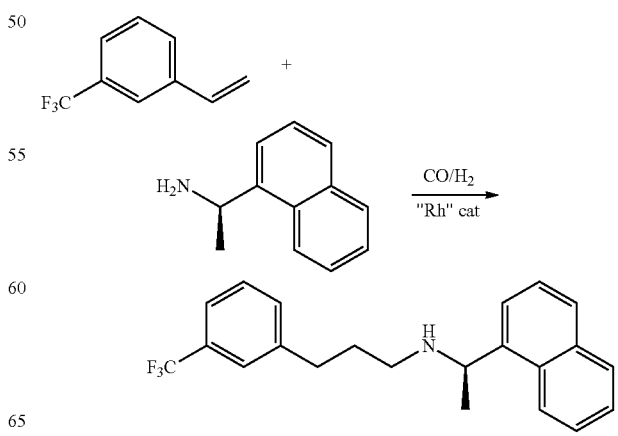

Accordingly, to a high pressure stainless steel reaction vessel (ChemScan Reactor System) was added 3-(trifluoromethyl)styrene (2.0 equiv.; 3.5 mmol; 0.520 mL), (R)-(+)-1-(1-Napthyl)ethylamine (1.0 equiv.; 1.75 mmol; 0.281 mL), Xantphos (4 mol %; 40.5 mg) and [Rh(cod)$_2$]BF$_4$ (1 mol %; 7.1 mg) in a mixture of toluene and methanol (1:1; 4 mL). The vessel was pressurized to 40 bar with SynGas (CO/H$_2$) and heated to 125° C. for 8 hours. A sample was prepared for analysis by diluting the reaction mixture prior to injection onto an HPLC system. Solution yield: 53.8%. The identity of the product was confirmed by RRT and LCMS (M+1): 358.1.

Example 6

Alkene Metathesis

The invention further provides a synthetic methodology for cinacalcet based on a metal catalyzed alkene metathesis reaction between a styrene analog and an acrylamide derivative. Accordingly, 3-(trifluoromethyl)styrene (1.0 equiv.; 0.44 mmol; 0.065 mL), N—((R)-1-naphthalen-1-yl-ethyl)-acrylamide (1.0 equiv.; 0.44 mmol; 100 mg) and Grubbs second generation catalyst (15 mol %; 56 mg) in toluene (0.5 mL) were added to a 10 mL flask equipped with a condenser. The mixture was stirred under an inert atmosphere at 85° C. for 7 hours. The solvent was removed in vacuo and the residue was diluted in a volumetric flask with methanol. Product identity was confirmed by RRT and LC/MS (M+1): 370.4. Percent solution yield based on the chromatogram was 6.9%.

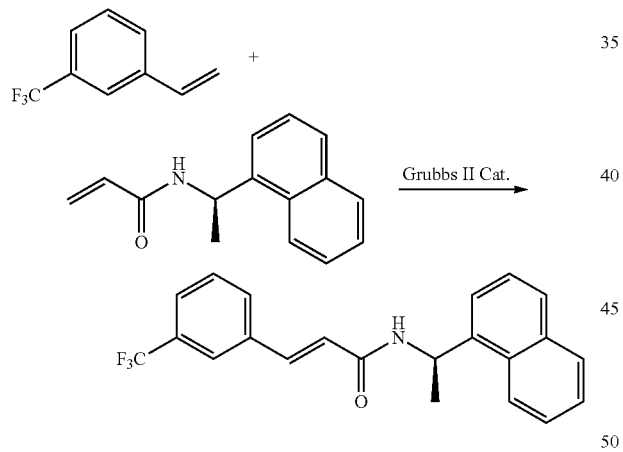

What is claimed is:

1. A method for the preparation of cinacalcet, a cinacalcet derivative, or a salt thereof, comprising:
   a) admixing a compound of formula (VIII) and a compound of formula (XI), under conditions that promote coupling of compound (VIII) and compound (XI) to form compound (XII)

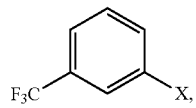
(VIII)

(XI)

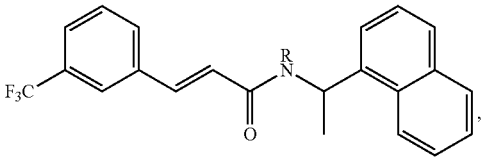
(XII)

wherein X is selected from the group consisting of chlorine, bromine, iodine, OSO$_2$C$_6$H$_4$CH$_3$, OSO$_2$CH$_3$, OSO$_2$CF$_3$, OSO$_2$C$_4$F$_9$ and N$_2^+$, and R is selected from the group consisting of hydrogen, benzyl, substituted benzyl, BOC, CBZ, and acetate; and
   b) reducing compound (XII) under conditions that permit reduction to form cinacalcet, a cinacalcet derivative, or a salt thereof.

2. The method of claim 1, wherein the conditions that promote coupling of compound (VIII) and compound (XI) comprise performing said coupling in the presence of a Pd catalyst or a Ru catalyst.

3. The method of claim 1, wherein the conditions that permit reduction comprise (a) performing said reduction in the presence of hydrogen and a Pd, Ni, Pt, Rh, Ru or Ir catalyst, (b) performing said reducing in the presence of borane or lithium aluminum hydride, or (c) a combination thereof.

4. The method of claim 1, wherein the product of said method is cinacalcet hydrochloride.

5. A method for the preparation of cinacalcet or a salt thereof comprising:
   a) admixing a compound of formula (I) and a compound of formula (XVIII) under conditions that permit cross-metathesis to produce a compound of formula (IV):

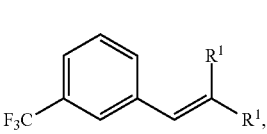
(I)

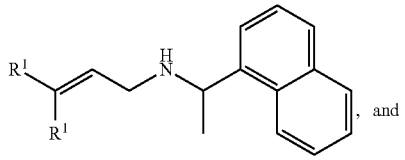
(XVIII)

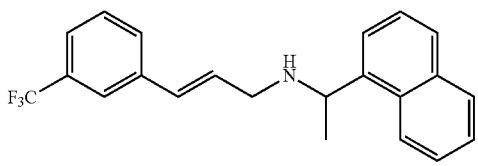
(IV)

wherein each R$^1$ is the same or different and is selected from the group consisting of hydrogen and C$_1$-C$_6$ alkyl; and
   b) reducing compound (IV) under conditions that permit reduction to produce cinacalcet or a salt thereof.

6. The method of claim 5, wherein the conditions that permit cross-metathesis comprise performing said cross-metathesis in the presence of a Ru or Mo catalyst.

7. The method of claim 5, wherein each $R^1$ is independently selected from hydrogen and methyl.

8. The method of claim 5, wherein the conditions that permit reduction in step (b) comprise performing said reduction in the presence of hydrogen and a Pd, Ni, Pt, Rh, Ru or Ir catalyst.

9. The method of claim 5, wherein the product of said method is cinacalcet hydrochloride.

10. A method for the preparation of cinacalcet or a salt thereof comprising:
 a) admixing a compound of formula (I) and a compound of formula (XIX) under conditions that permit cross-metathesis to produce a compound of formula (VIIB):

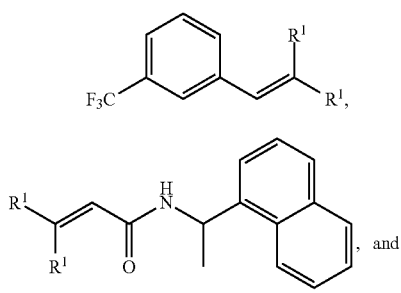

(I)

(XIX)

, and

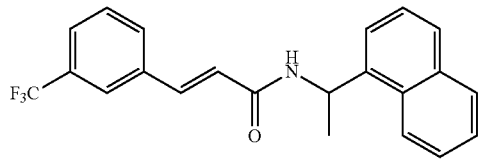

(VIIB)

wherein each $R^1$ is the same or different and is selected from the group consisting of hydrogen and $C_1$-$C_6$ alkyl; and
 b) reducing compound (VIIB) under conditions that permit reduction to produce cinacalcet or a salt thereof.

11. The method of claim 10, wherein the conditions that permit cross-metathesis comprise performing said cross-metathesis in the presence of a Ru or Mo catalyst.

12. The method of claim 10, wherein each $R^1$ is independently selected from hydrogen and methyl.

13. The method of claim 10, wherein the conditions that permit reduction in step (b) comprise (1) performing said reduction in the presence of hydrogen and a Pd, Ni, Pt, Rh, Ru or Ir catalyst, (2) performing said reducing in the presence of borane or lithium aluminum hydride, or (3) a combination thereof.

14. The method of claim 10, wherein the product of said method is cinacalcet hydrochloride.

* * * * *